United States Patent
Won et al.

(10) Patent No.: US 11,173,491 B2
(45) Date of Patent: Nov. 16, 2021

(54) APPARATUS FOR HIGH-SPEED NUCLEIC ACID AMPLIFICATION AND METHOD FOR TEMPERATURE CONTROL OF NUCLEIC ACID AMPLIFICATION REACTION

(71) Applicants: U-GENE & CELL CO., Seoul (KR); BODITECH MED INC., Chuncheon-si (KR)

(72) Inventors: Byoung Yeon Won, Seoul (KR); Sanghyun Park, Seoul (KR); Youn Tae Im, Chuncheon-si (KR); Jae Un An, Incheon (KR); Bong Kyu Lee, Seoul (KR); Jae-ho Lee, Chuncheon-si (KR); Hanseung Jeong, Seoul (KR)

(73) Assignees: U-GENE & CELL CO., Seoul (KR); BODITECH MED INC., Chuncheon-si (KR)

( * ) Notice: Subject to any disclaimer, the term of this patent is extended or adjusted under 35 U.S.C. 154(b) by 164 days.

(21) Appl. No.: 16/473,015

(22) PCT Filed: Jan. 12, 2018

(86) PCT No.: PCT/KR2018/000588
§ 371 (c)(1),
(2) Date: Jun. 24, 2019

(87) PCT Pub. No.: WO2018/139788
PCT Pub. Date: Aug. 2, 2018

(65) Prior Publication Data
US 2019/0329261 A1    Oct. 31, 2019

(30) Foreign Application Priority Data

Jan. 25, 2017 (KR) .................. 10-2017-0011674
Feb. 3, 2017 (KR) .................. 10-2017-0015335

(51) Int. Cl.
*B01L 7/00* (2006.01)
*B01L 9/06* (2006.01)
*C12Q 1/6848* (2018.01)

(52) U.S. Cl.
CPC .................. *B01L 7/52* (2013.01); *B01L 7/54* (2013.01); *B01L 9/06* (2013.01); *C12Q 1/6848* (2013.01);
(Continued)

(58) Field of Classification Search
CPC .. B01L 7/52; B01L 7/54; B01L 7/5255; B01L 9/06; B01L 2200/022;
(Continued)

(56) References Cited

U.S. PATENT DOCUMENTS 5,578,270 A    11/1996  Reichler et al.
9,765,383 B2    9/2017  Park et al.
(Continued)

FOREIGN PATENT DOCUMENTS

CN        102533525 A    7/2012
CN        103820306 A    5/2014
(Continued)

OTHER PUBLICATIONS

Wittwer, C.T., et al., "The LightCyclerÔ: A Microvolume Multisample Fluorimeter with Rapid Temperature Control," Bio Techniques, vol. 22, Issue 1, pp. 176-181 (1997).
(Continued)

*Primary Examiner* — Michael L Hobbs
(74) *Attorney, Agent, or Firm* — Maschoff Brennan

(57) ABSTRACT

The present invention relates to an apparatus for nucleic acid amplification and, more particularly, to an apparatus for nucleic acid amplification capable of rapid nucleic acid amplification by rapidly heating and cooling a reactant in a reaction vessel for a chemical/biochemical reaction requiring a temperature change, and a method for temperature control in nucleic acid amplification.

34 Claims, 33 Drawing Sheets

(52) U.S. Cl.
CPC ... *B01L 2200/022* (2013.01); *B01L 2200/147* (2013.01); *B01L 2300/0681* (2013.01); *B01L 2300/1805* (2013.01)

(58) Field of Classification Search
CPC ....... B01L 2200/147; B01L 2300/0681; B01L 2300/1805; B01L 2300/1827; B01L 2300/1822; B01L 2300/185; B01L 2300/1844; B01L 3/50855; C12Q 1/686; C12Q 1/6844; C12Q 1/689; C12Q 1/6853; C12Q 1/6848
See application file for complete search history.

(56) References Cited

U.S. PATENT DOCUMENTS

2008/0038163 A1* 2/2008 Boege ................. B01L 7/52
422/600

2008/0176290 A1* 7/2008 Joseph ................. B01L 7/5255
435/91.2

FOREIGN PATENT DOCUMENTS

| | | |
|---|---|---|
| JP | 08-117590 A | 5/1996 |
| JP | 08-266267 A | 10/1996 |
| JP | 2002-306154 A | 10/2002 |
| JP | 5381100 B2 | 1/2014 |
| KR | 10-2013-0092185 A | 8/2013 |
| WO | 2008/102772 A1 | 8/2008 |

OTHER PUBLICATIONS

Wittwer, C.T., et al., "Minimizing the time required for DNA amplification by efficient heat transfer to small samples," Analytical Biochemistry, vol. 186, Issue 2, pp. 328-331 (May 1, 1990).

Wittwer, C.T. et al., The PCR Revolution: Basic technologies and applications edited by Stephen A. Bustin, "Chapter 4: Rapid polymerase chain reaction and melting analysis" pp. 48-69 (Jan. 2009).

* cited by examiner

APPARATUS FOR HIGH-SPEED NUCLEIC ACID AMPLIFICATION AND METHOD FOR TEMPERATURE CONTROL OF NUCLEIC ACID AMPLIFICATION REACTION

TECHNICAL FIELD

The present invention relates to an apparatus for a high-speed nucleic acid amplification which is capable of rapidly heating and cooling a reactant in a reaction vessel for a chemical or biochemical reaction requiring a change in temperature and a technology capable of rapidly raising and lowering a reaction temperature for a chemical or biochemical reaction requiring a change in temperature.

BACKGROUND ART

A polymerase chain reaction (PCR) is a technology capable of selectively amplifying a specific nucleic acid in a biological sample, for example. In this process, a reactant containing the sample usually requires repetitive heating and cooling of several tens of times. One of important factors that determine the overall reaction time in a nucleic acid amplification reaction is a time taken to heat a reactant to a predetermined temperature or to cool the reactant to a predetermined temperature. Thus, an apparatus used in this method is provided with a module capable of periodically raising and lowering the temperature and has been developed in terms of improvement in the precision and/or speed of temperature control.

In recent years, since nucleic acid amplification has been used for the processing of a large number of samples in the fields of agriculture, animal husbandry, environment, and medicine, according to this tendency, there is a demand for the development of an apparatus capable of rapidly performing a reaction at a high speed.

In intracellular and extracellular chemical and biochemical reactions, temperature is one of crucial factors that affect desired results and it may occasionally be necessary to repeatedly control the temperature according to the type of a specific reaction. For example, a typical nucleic acid amplification method such as a polymerase chain reaction (PCR) is a technology capable of selectively amplifying a specific nucleic acid in a biological sample, for example. In this process, a reaction solution containing the sample usually requires repetitive heating and cooling of several tens of times.

Conventionally, an important technical challenge in a nucleic acid amplification reaction was to improve the specificity of target detection and the sensitivity for detecting a small amount of target. However, according to the recent tendency of using nucleic acid amplification for the processing of a large number of samples in the fields of agriculture, animal husbandry, environment, and medicine, shortening the overall reaction time of nucleic acid amplification has emerged as an important challenge.

In a PCR which is a typical nucleic acid amplification reaction, a target nucleic acid is usually amplified by repeating heating and cooling about 25 to 40 times within a temperature range of 55° C. to 95° C. The overall reaction time may be controlled when the time of a heating-cooling cycle is controlled.

Temperature control apparatuses (e.g., a PCR thermocycler), which adopt a thermoelectric element (e.g., Peltier element), hot air and cold air, or a heater and a blower, for example, has conventionally been used for such repetitive heating and cooling in the PCR.

A temperature control technology using a thermoelectric element is currently the most commonly used technology for a PCR apparatus. Such an apparatus performs a PCR by fixedly mounting a reaction vessel to a metal block and repeatedly heating and cooling the block using a thermoelectric element. Such a method, however, requires a complicated circuit for precise temperature control, although the overall structure of the apparatus is simplified, and since one block is repeatedly heated and cooled, a large amount of time is required to allow the block to repeatedly reach a preset heating or cooling temperature preferentially, in addition to heat exchange occurring between the block as a heating or cooling source and a sample in the reaction vessel, which disadvantageously causes a longer time for the entire reaction.

A method using hot air and cold air is a technology applied to a Roche Lightcycler® PCR system. In this method, an airflow which has passed through a heating coil to reach a specific temperature is brought into contact with a reaction vessel to induce a change in the temperature of a sample in the reaction vessel (Wittwer et al. in Anal Biochem. 186, 328-331, 1990 & Wittwer et al. in BioTechniques, 22, 176-181, 1997). However, there is a need for a technology of controlling hot air to realize uniform heat exchange with a plurality of reaction vessels, and since the time for a change in the temperature of the heating coil is preferentially required in addition to the time for heat exchange between a heating source and a sample, similar to the technology using a thermoelectric element, this method is far from a rapid temperature control technology for shortening the reaction time.

As another method, a heat exchange method using a resistance heater and a blower has been reported. In this method, a reaction proceeds in a state in which a reaction vessel is in close contact with and fixed to the resistance heater, and a process of heating a sample in the reaction vessel by raising the temperature of the heater, and then lowering the temperature of the reaction vessel by blowing air while the heater is powered off is repeated. This method also does not meet the purpose of rapid temperature control for shortening the reaction time because the time for the heating of the heater is repeatedly required.

A reduction in PCR time allows a PCR-based inspection method to be applied to an actual field, which may play an important role in enabling a rapid response to rapidly spreading infectious diseases such as recent variant virus outbreaks. Therefore, there is a high demand for the development of an effective temperature control method that may shorten the entire PCR time by minimizing time consumption during a temperature variation period of nucleic acid amplification.

DISCLOSURE

Technical Problem

It is one object of the present invention to provide an apparatus for high-speed nucleic acid amplification which is capable of rapidly heating and cooling a reactant in a reaction vessel in a nucleic acid amplification reaction requiring repetitive temperature change, thus enabling rapid nucleic acid amplification.

In addition, it is another object of the present invention to provide a method capable of rapidly heating or cooling a reactant in a reaction vessel in a nucleic acid amplification reaction requiring repetitive temperature change.

Technical Solution

In accordance with one aspect of the present invention, provided is a nucleic acid amplification apparatus which is capable of rapidly controlling the temperature of a reactant or a reaction solution that undergoes an amplification reaction to enable high-speed nucleic acid amplification, the apparatus includes a holder configured to fix a position of a tube in which the reactant is accommodated, a heating module configured to heat the reactant, a drive module configured to move the heating module or the holder so as to vary a distance between the heating module and the holder, and a cooling module configured to cool the tube located in the holder.

The heating module may include a heater configured to generate heat and a heating block connected to the heater, the heating block may be heated by the heater, the heating block may include at least one recess formed to allow at least a portion of the tube to be introduced thereinto, and the drive module may move the holder or the heating module to vary a distance between the recess and the tube.

The heating block may be disposed below the holder, the drive module may vertically move the heating block, the holder may have at least one mounting hole vertically formed in the holder and having a predetermined inner diameter, the tube may be mounted in the mounting hole so that a lower portion of the tube is exposed downward, the lower portion of the tube may be introduced into the recess when the heating block is raised, and the lower portion of the tube may be spaced apart from the recess so as to be exposed when the heating block is lowered.

The heating module may further include a guide unit disposed on a side of the heater, and the guide unit may include a guide pipe having a hole vertically formed therein, a guide beam inserted into the hole in the guide pipe to vertically extend, and an elastic spring located on the guide pipe so that the guide beam is inserted thereinto.

The cooling module may include a blower fan configured to generate a cooling airflow and a blower nozzle configured to transfer the cooling airflow generated by the blower fan to the tube fixed to the holder, and the blower nozzle may be closed when the heating module is disposed adjacent to the holder and may be opened when the heating module is spaced apart from the holder.

The heating module may be disposed below the holder, the drive module may vertically move the heating module, the blower nozzle may be disposed on one lateral side of the holder, the heating module may include an opening and closing block, the opening and closing block may include a shield, the shield may close the blower nozzle when the heating module is raised and may be downwardly spaced apart from the blower nozzle to open the blower nozzle when the heating module is lowered.

The holder may include a plurality of mounting holes arranged in parallel to form one or more alignment lines, the blower nozzle may include an inlet adjacent to the blower fan and an outlet adjacent to the holder, the outlet may have a horizontal width wider than a horizontal width of the inlet, the outlet of the blower nozzle may be horizontally disposed outside the holder, and a width direction of the outlet may be arranged parallel to the lines of the mounting holes.

The apparatus may further include a sensing module configured to sense a reaction signal of a reactant in the tube and a cover module disposed on the holder and configured to be opened or closed, the cover module may include a light source configured to provide light to the tube, and the sensing module may include a sensor configured to sense the light generated in the reactant in the tube.

The cover module may further include an excitation filter disposed below the light source, and the sensing module may further include an emission filter disposed between the tube and the sensor.

The heating block may include a light transmitting portion formed in at least one direction so that the light generated in the tube is transmitted in at least one lateral direction.

The apparatus may further include a control device configured to control operations of the heating module, the drive module, and the cooling module.

In another aspect of the present invention, provided is a method of adjusting or controlling a temperature of a nucleic acid amplification reaction in which denaturation performed at a first temperature and an annealing and extension reaction performed at a second temperature are repeated multiple times, the method including heating a vessel used for the nucleic acid amplification reaction to a first temperature by bringing the vessel into contact with a heating block consistently maintained at the first temperature for a predetermined time and cooling the vessel to a second temperature by separating the vessel from the heating block by a predetermined distance so that the separated vessel is exposed to an artificial airflow at room temperature for a predetermined time, the heating and the cooling being repeated multiple times with respect to the vessel cooled to the second temperature.

In one embodiment of the method according to the present invention, in the cooling, the heating block may be at a fixed position, and the vessel may be moved upward of the heating block to a predetermined position so as to realize the predetermined distance. In this case, the artificial airflow may be continuously provided.

In another embodiment of the method according to the present invention, in the cooling, the vessel may be at a fixed position, and the heating block may be moved downward of the vessel to a predetermined position so as to realize the predetermined distance. In this case, the artificial airflow may be provided only when the heating block is spaced apart from the vessel by a predetermined distance via an opening and closing device, for example.

In the method according to the present invention, the second temperature ranges from 55° C. to 65° C. to cause annealing and extension to occur at the same time.

In a further aspect of the present invention, provided is a method of controlling a temperature in a nucleic acid amplification reaction in which one cycle consisting of denaturation performed at a first temperature, annealing performed at a second-first temperature, and extension performed at a second-second temperature is repeated multiple times.

The method includes heating a vessel used for the nucleic acid amplification reaction to a first temperature by bringing the vessel into contact with a heating block consistently maintained at the first temperature for a predetermined time, cooling the vessel to the second-first temperature by separating the vessel from the heating block by a predetermined distance so that the separated vessel is exposed to an artificial airflow for a predetermined time, and heating the vessel to the second-second temperature by bringing the vessel into contact with the heating block for a predetermined time, and then separating the vessel from the heating block by a predetermined distance to cause the separated vessel to remain stationary in air for a predetermined time.

In one embodiment, when the vessel and the heating block are separated from each other by the predetermined distance, the heating block may be at a fixed position, and the vessel may be moved upward of the heating block to a predetermined position so as to realize the predetermined distance. In this case, the artificial airflow may be continuously provided.

In another embodiment, when the vessel and the heating block are separated from each other by the predetermined distance, the vessel may be at a fixed position, and the heating block may be moved downward of the vessel to a predetermined position so as to realize the predetermined distance. In this case, the artificial airflow may be provided only when the heating block is spaced apart from the vessel by a predetermined distance.

In all of the methods, the predetermined distance is a distance at which the reaction vessel may be separated from the heating block so as to be sufficiently cooled, and may be determined in consideration of the position thereof with respect to a cooling device. In particular, the predetermined distance may range from 0.5 cm to 2 cm.

Advantageous Effects

According to the present invention, the temperature of reactant may be rapidly controlled. That is, a tube in which the reactant is accommodated may be brought into contact with a heating block of a heating module so as to be rapidly heated. When the heating is sufficiently performed, the tube is separated from the heating block and the blower nozzle is opened so that the reactant may be rapidly cooled by a cooling airflow generated by a blower fan.

In addition, when the operation of the heating module is set according to user intention, the heating time and the cooling time of the reactant may be controlled so that the reactant reaches any of various target temperatures, and a target temperature range may be maintained. For example, when the operation cycle of the heating module is changed or when the time during which the heating module is maintained at the raised position thereof or the time during which the heating module is maintained at the lowered position thereof are set differently, the heating time and cooling time of the reactant may be set differently, whereby the temperature of the reactant may be easily controlled as desired by the user.

In addition, the heating and cooling of the reactant may be achieved with a very simple operation. That is, when the heating block and an opening and closing block provided in the heating module are raised and lowered together at the time of heating, the heating block may approach the tube to perform rapid heating and the opening and closing block may close the blower nozzle to prevent cooling by the cooling airflow. In addition, at the time of cooling, the heating block is spaced apart from the tube to stop the heating and the opening and closing block is spaced apart from the blower nozzle to open the blower no so that rapid cooling by the cooling airflow is achieved. In this way, heating and cooling may be appropriately and rapidly performed only by an operation signal for the drive module which moves the heating module without requiring the input of a separate cooling operation signal.

In addition, in the heating process, the light generated in a light source of a cover module is incident on the reactant in the tube and the light generated in the reactant is transmitted to and sensed by a sensor, whereby the reaction result of the reactant may be detected in real time.

Accordingly a polymerase chain reaction (PCR), which is a typical chemical or biochemical reaction requiring temperature control for heating and cooling at a predetermined interval may be rapidly performed.

In addition, according to the present invention heating and cooling in the nucleic acid amplification reaction may be performed rising separate devices so that the temperature of the reactant may be rapidly controlled. That is, when a vessel in which the reactant is accommodated comes into contact with the heating block maintained at a constant temperature so as to be rapid heated and such heating is sufficiently performed to a predetermined temperature the vessel may be separated from the heating block and the reactant may be rapidly cooled by the cooling airflow generated by the blower fan.

In addition, when the heating time and the cooling time of the reactant may be controlled according to user intention, control may be performed so that the temperature of the reactant may reach any of various target temperatures, and a target temperature range may be maintained.

Accordingly, a polymerase chain reaction (PCR), which is a typical chemical and biochemical reaction requiring temperature control for heating and cooling at constant interval may be performed quickly.

MODE FOR INVENTION

Hereinafter, exemplary embodiments of the present invention will be described with reference to the accompanying drawings. The embodiments are illustrative and are not intended to limit the present invention in any way.

Figure 1:
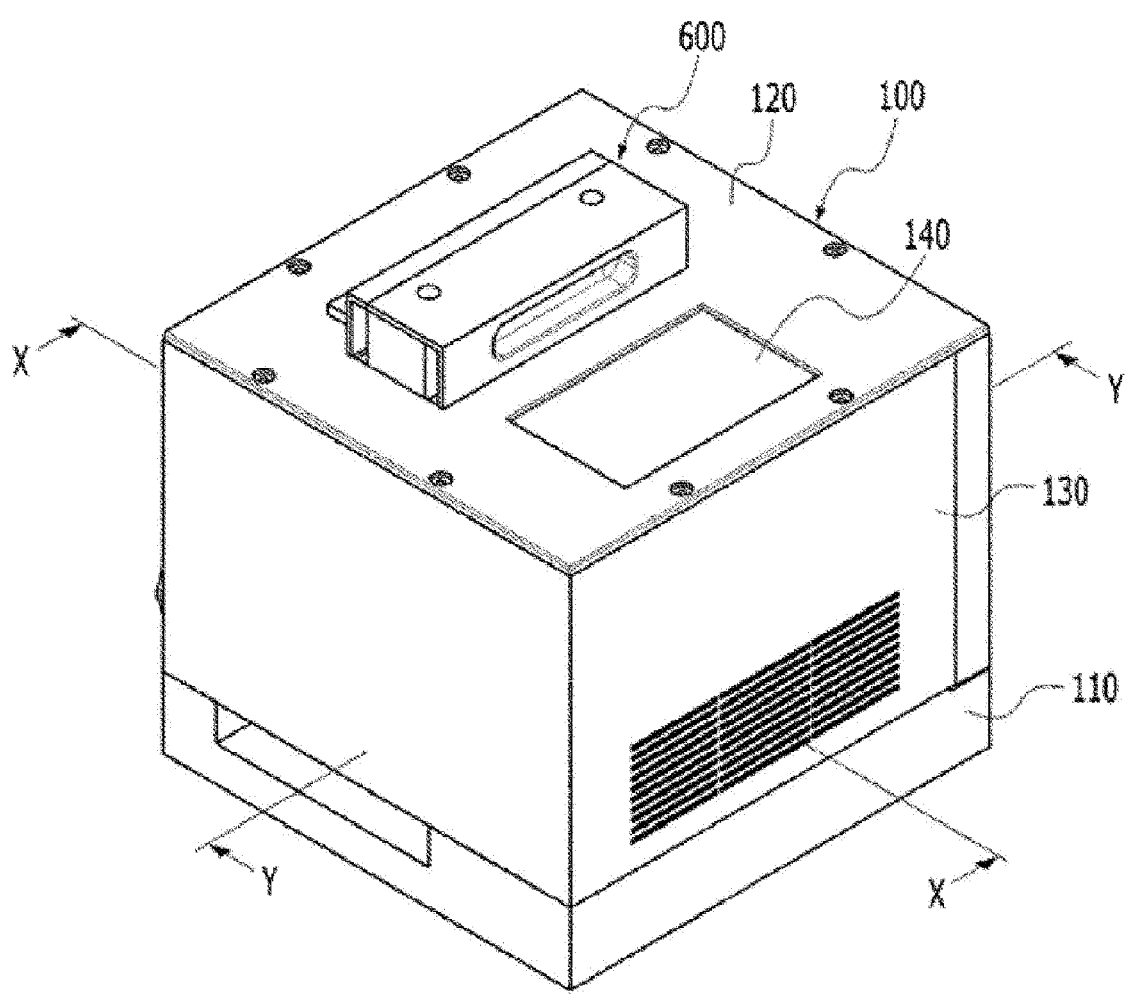
FIGS. 1 and 2 are views illustrating the external appearance of a nucleic acid amplification apparatus according to the present invention.
Figure 2:
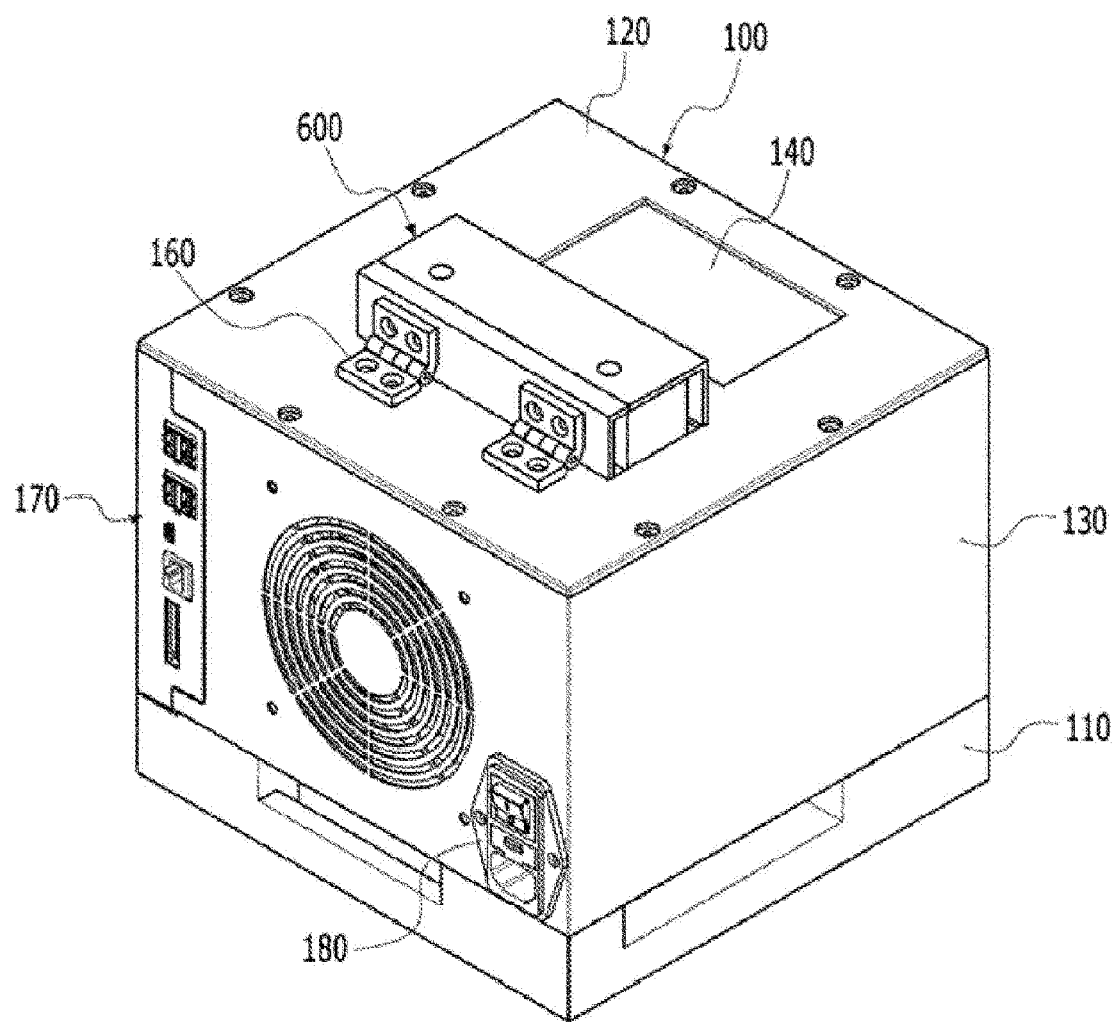
Figure 3:
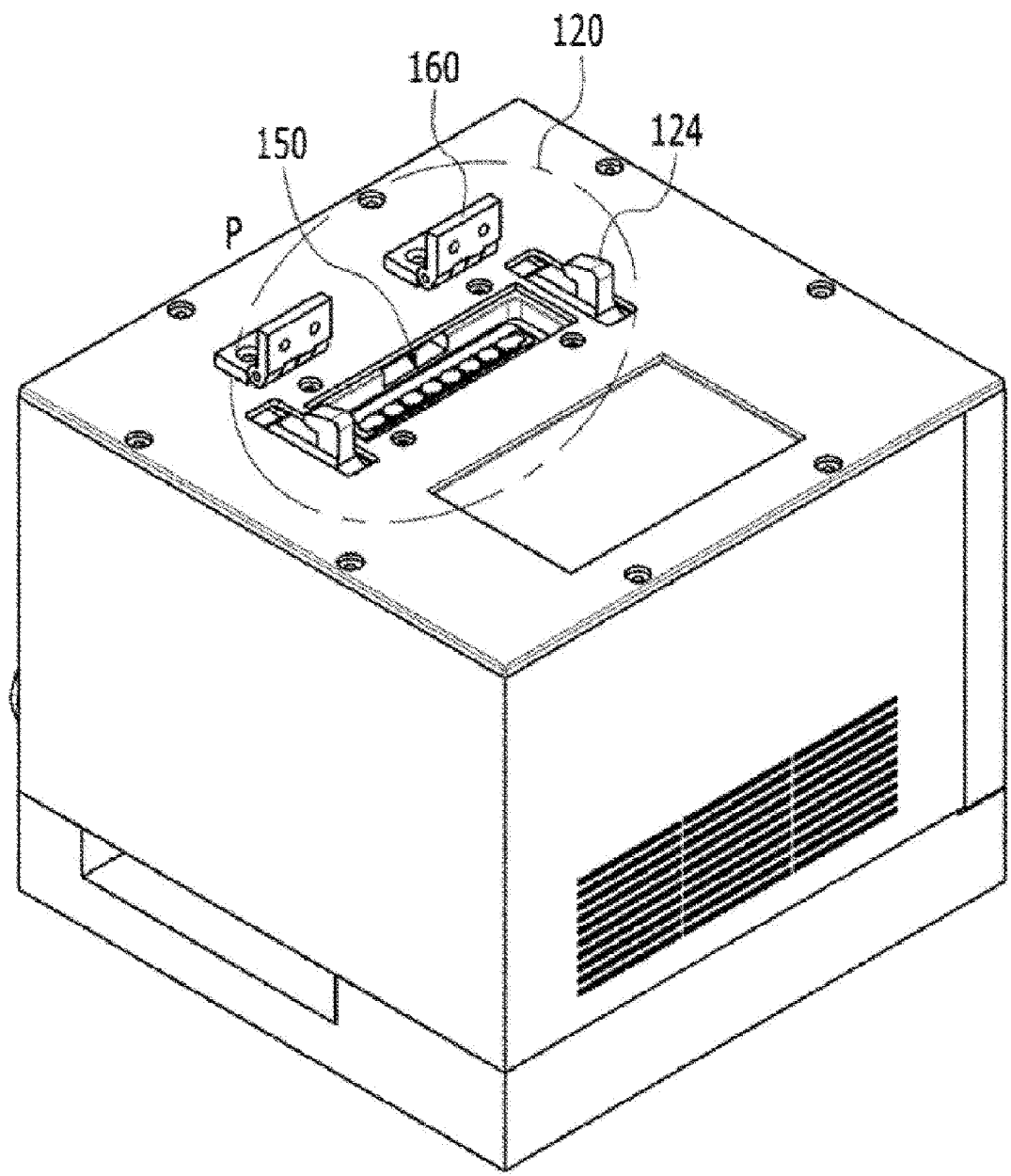
FIG. 3 is a view illustrating the state in which a cover module on a casing is removed from the nucleic acid amplification apparatus according to the present invention.
Figure 4:
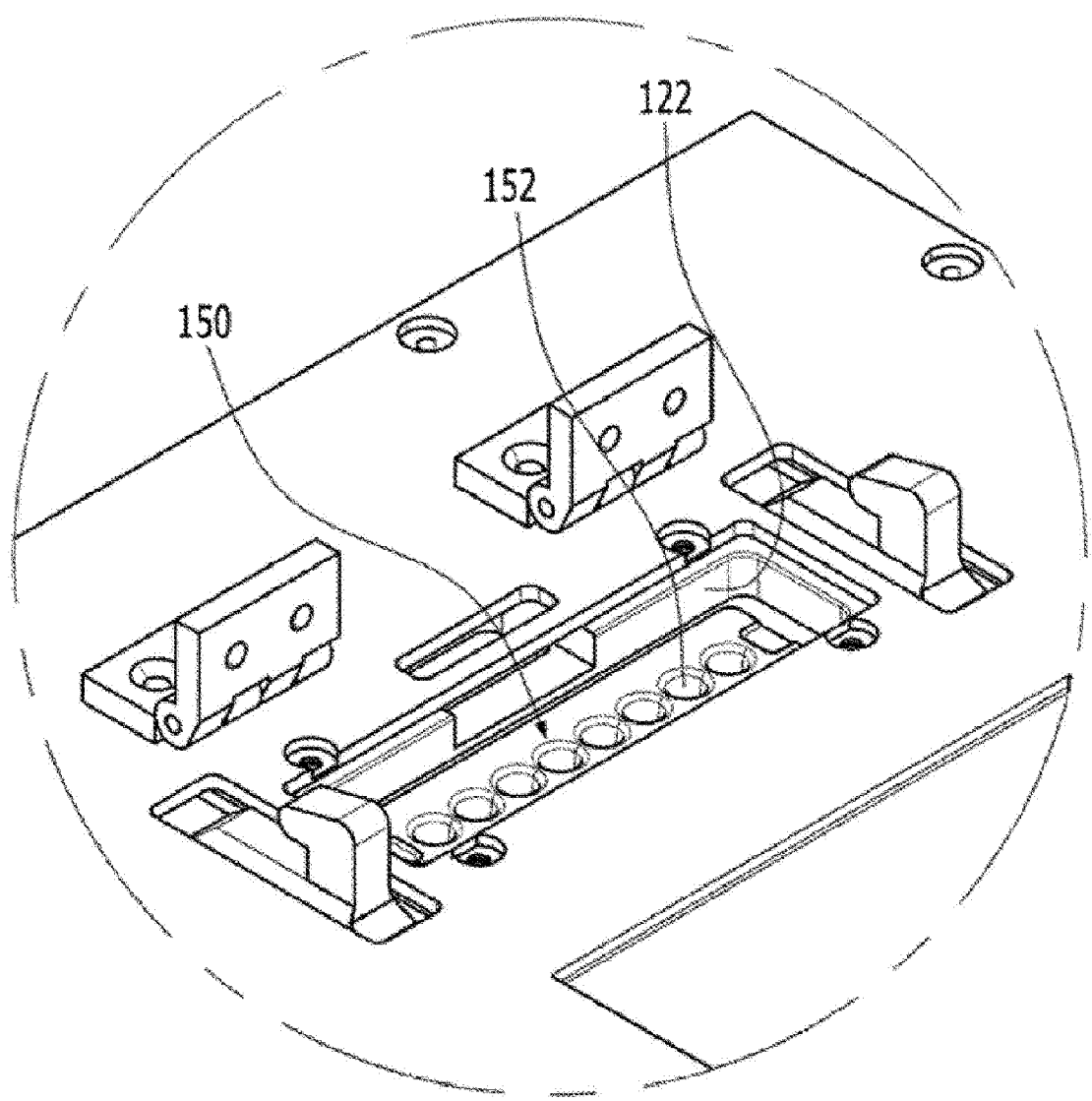
FIG. 4 is an enlarged view of portion P in FIG. 3.
Figure 5:
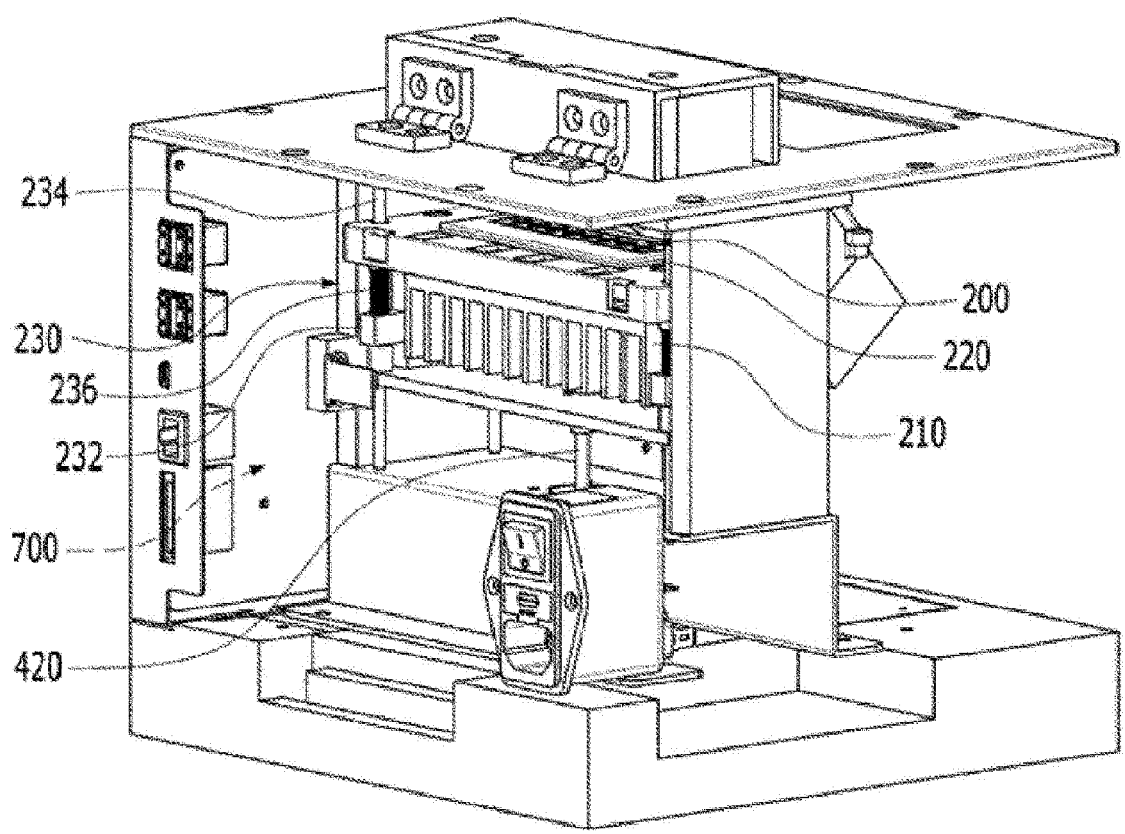
FIGS. 5 and 6 are views illustrating the state in which a side plate of the casing is removed from the nucleic acid amplification apparatus according to the present invention.
Figure 6:
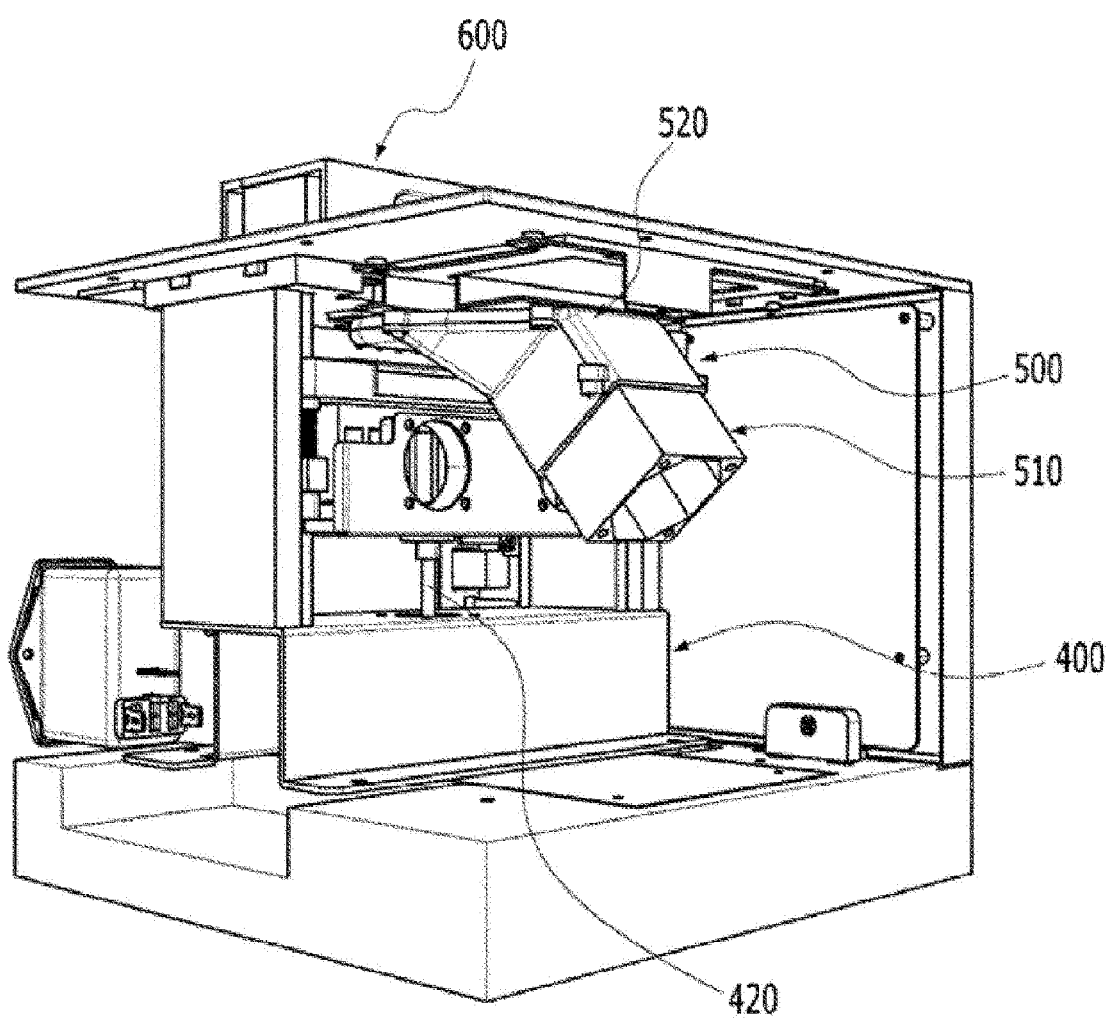
Figure 7:
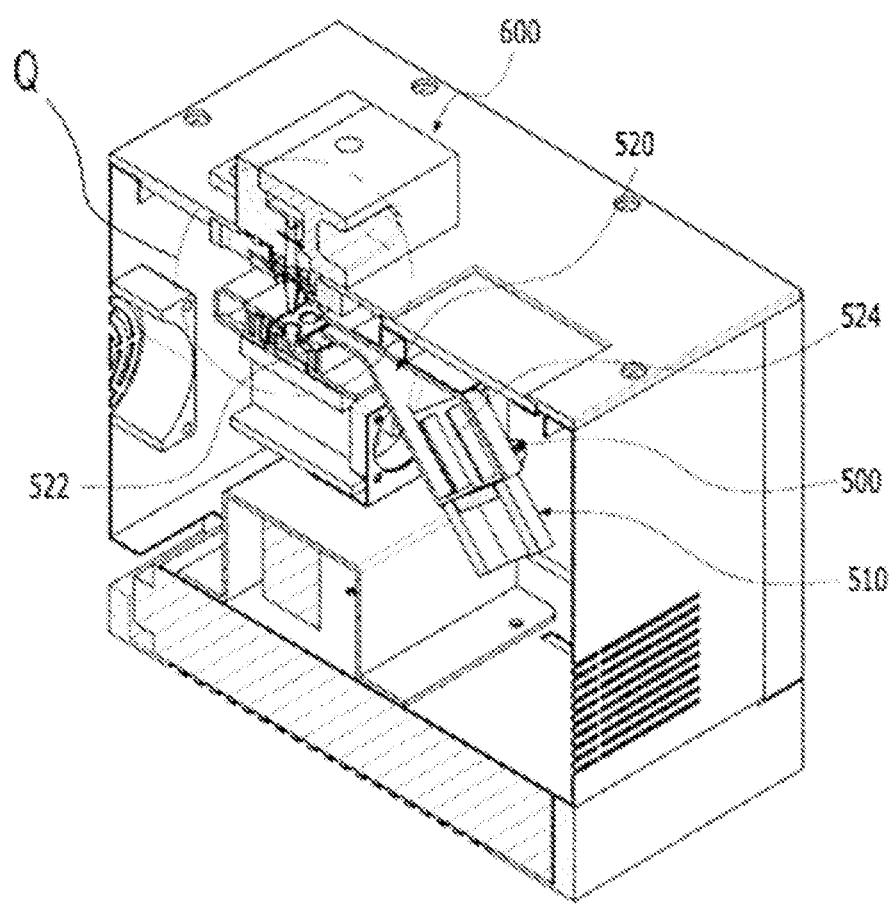
FIG. 7 is a view illustrating the cross section of the nucleic acid amplification apparatus according to the present invention.
Figure 8:
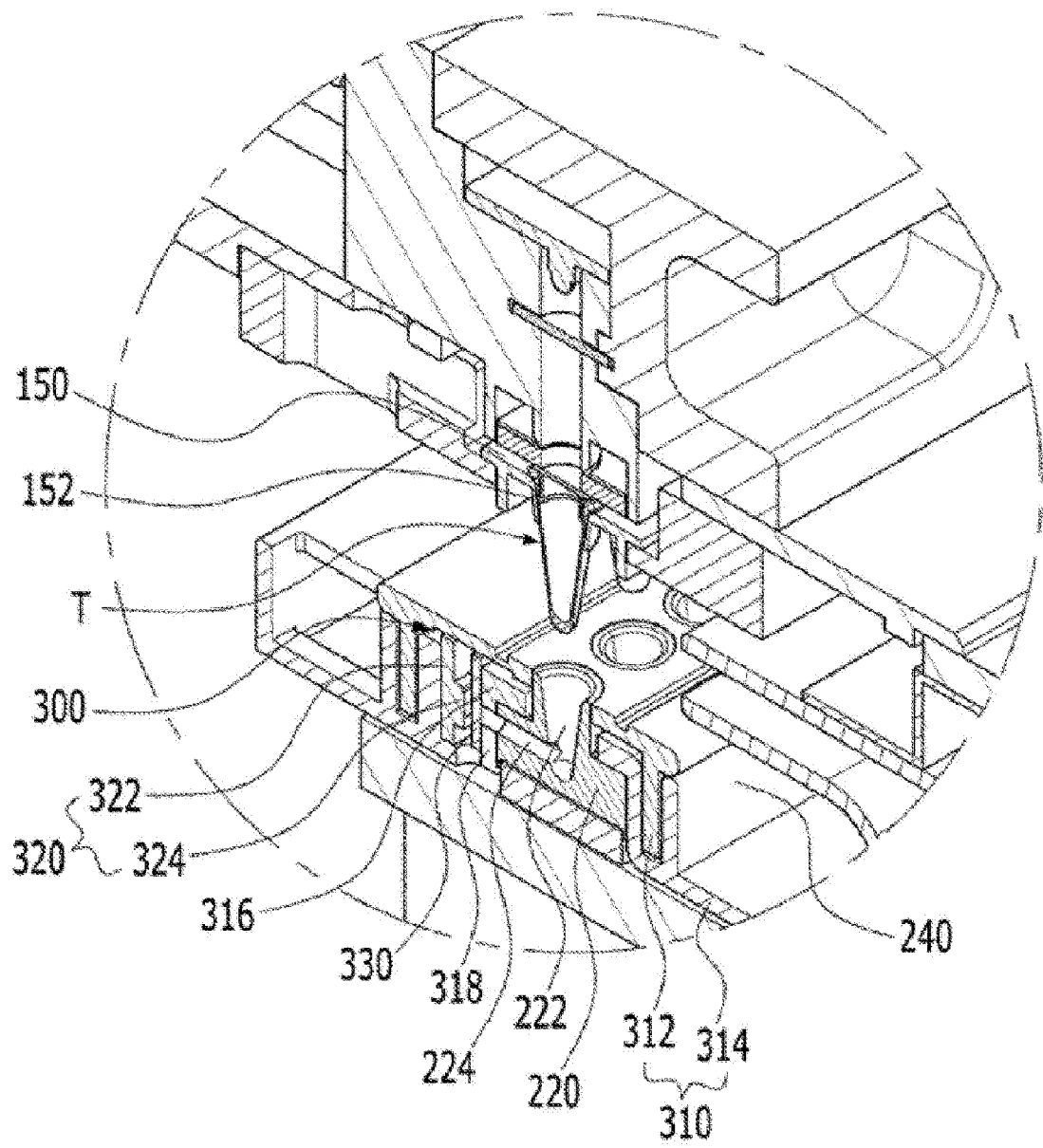
FIG. 8 is an enlarged view of portion Q in FIG. 7.
Figure 9:
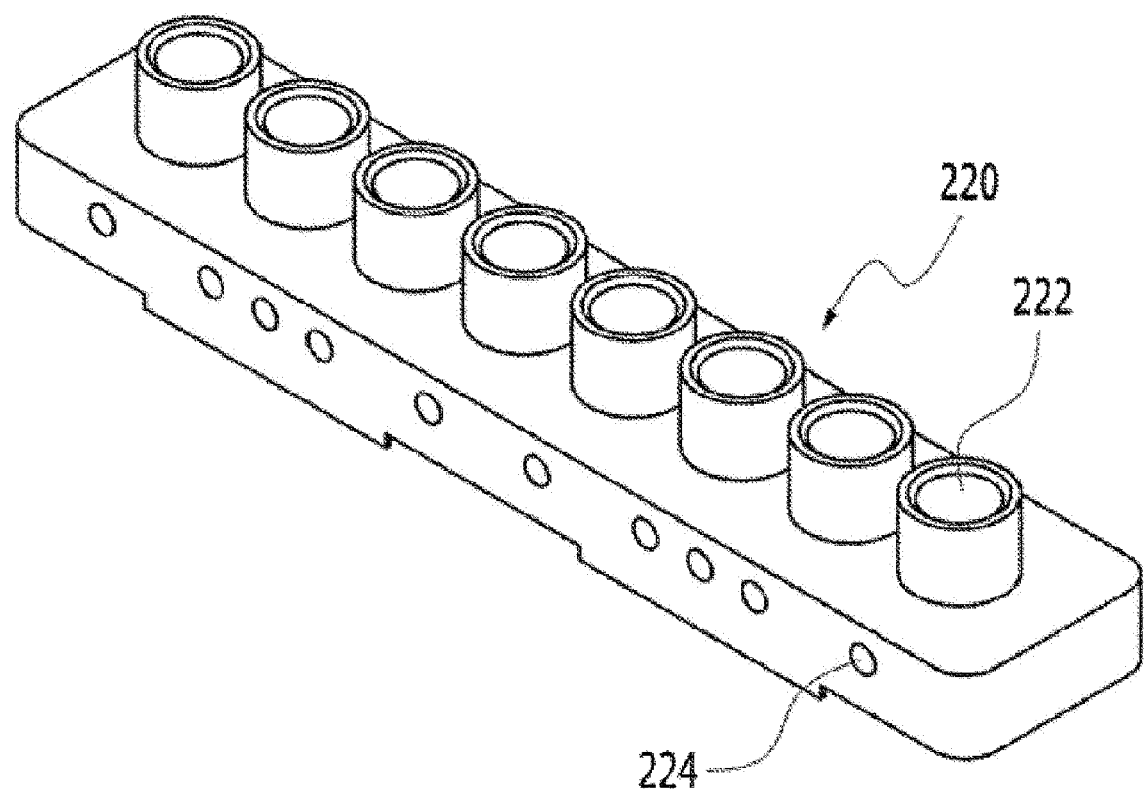
FIG. 9 is a view illustrating a heating block of the nucleic acid amplification apparatus according to the present invention.
Figure 10:
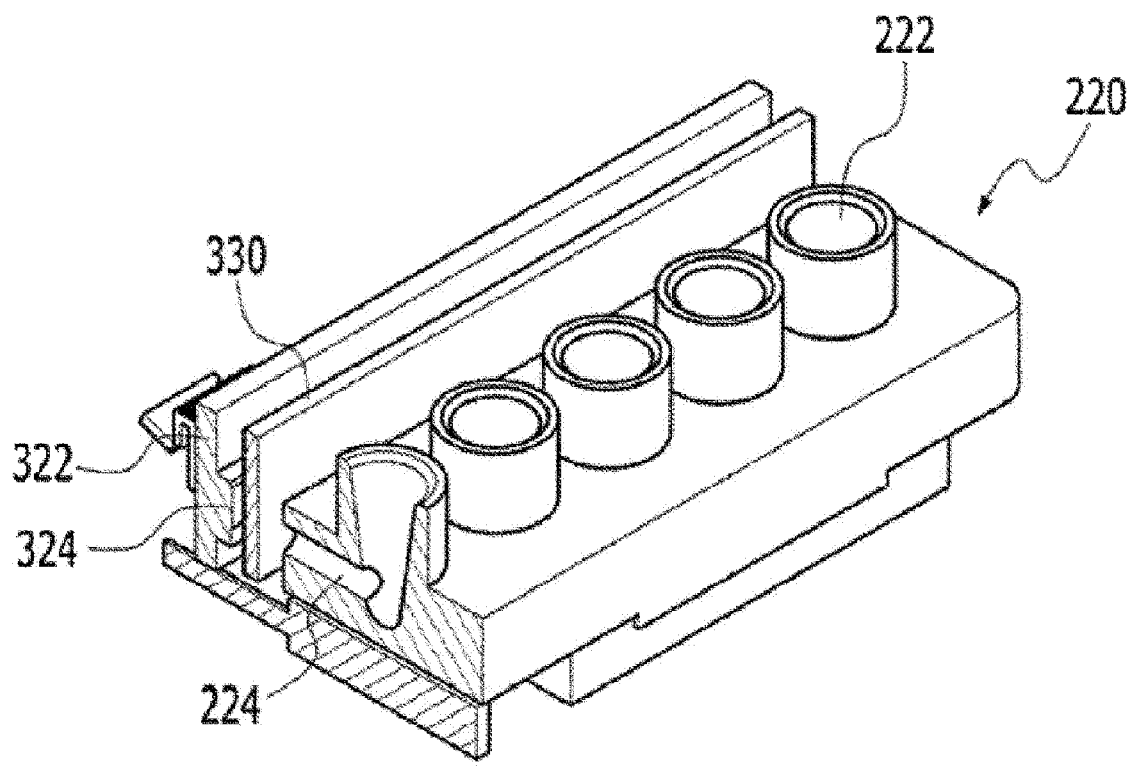
FIG. 10 is a view illustrating the positional relationship between the heating block and a sensing module of the nucleic acid amplification apparatus according to the present invention.
Figure 11:
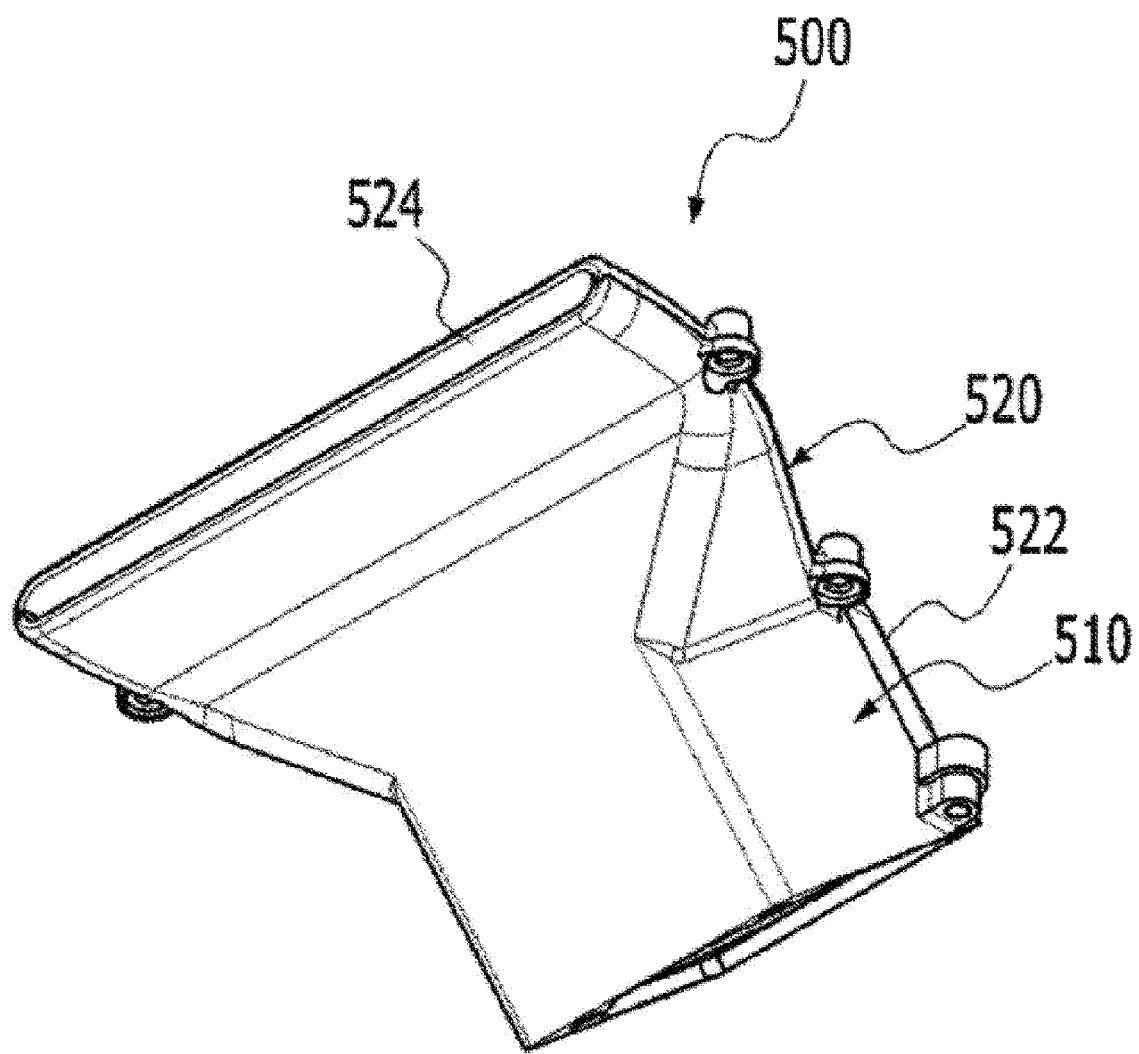
FIG. 11 is a view illustrating a blower nozzle of the nucleic acid amplification apparatus according to the present invention.
Figure 12:
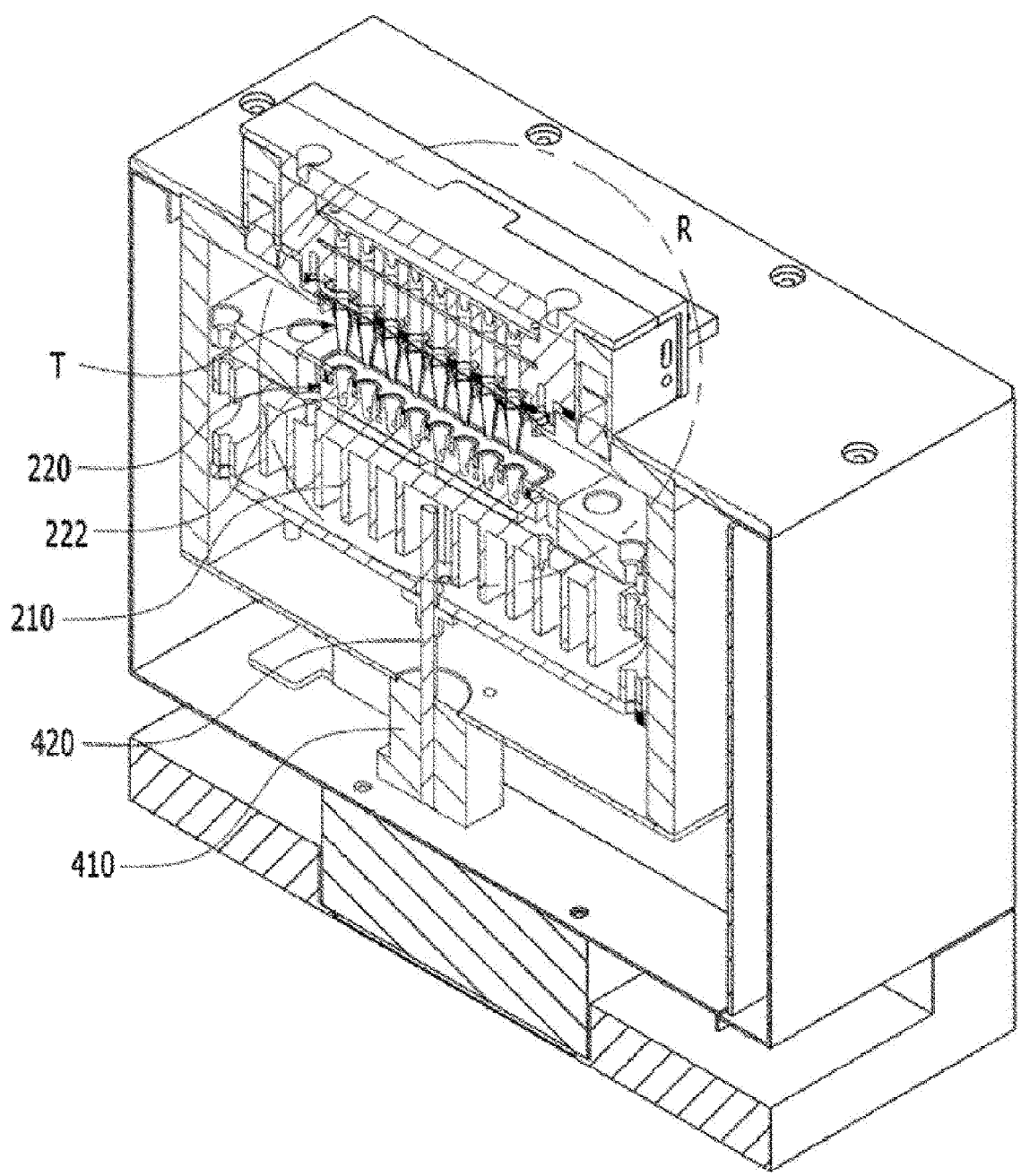
FIG. 12 is a view illustrating the cross section of the nucleic acid amplification apparatus according to the present invention.
Figure 13A:
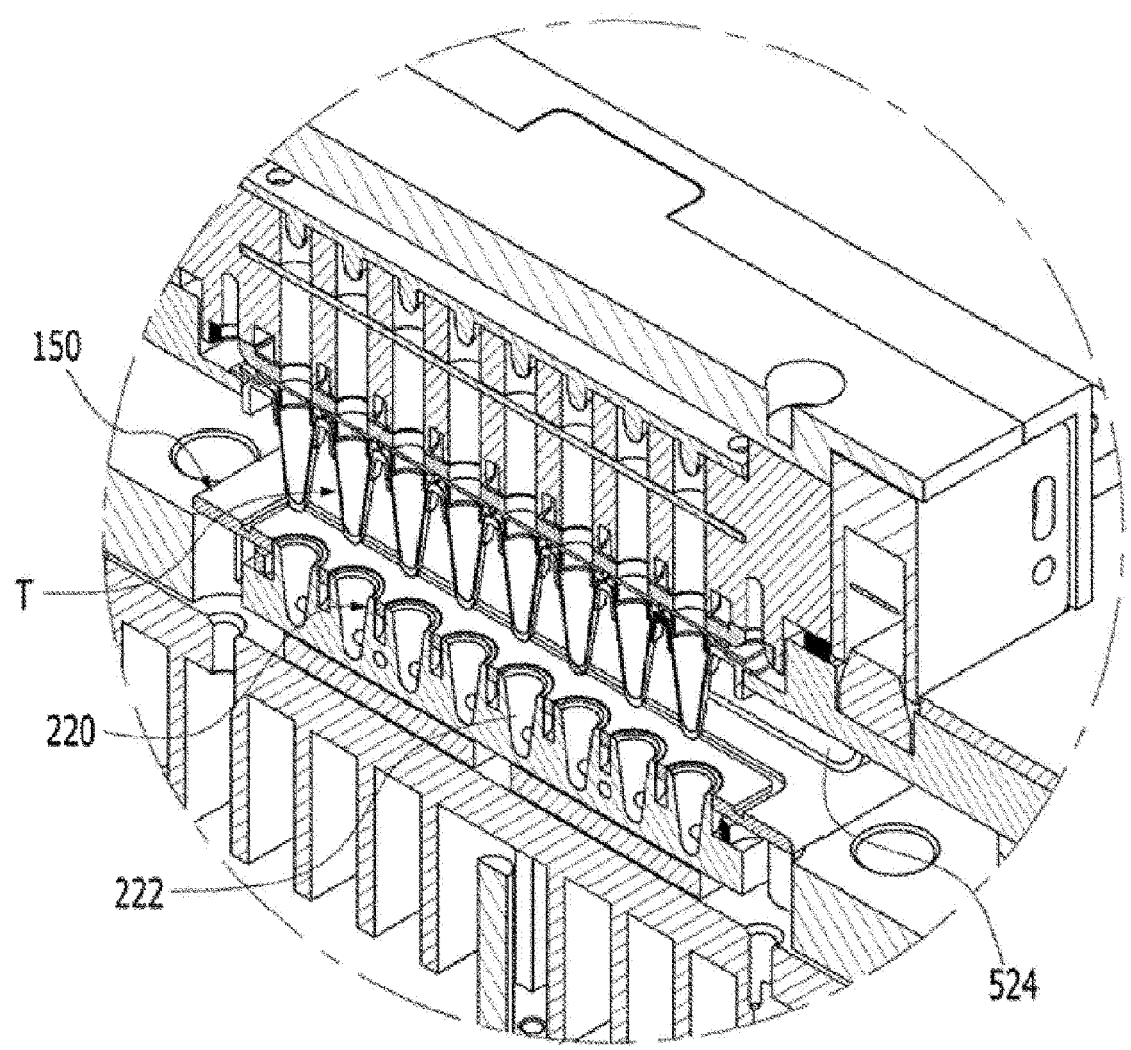
FIG. 13A is an enlarged view of portion R in FIG. 12.
Figure 13B:
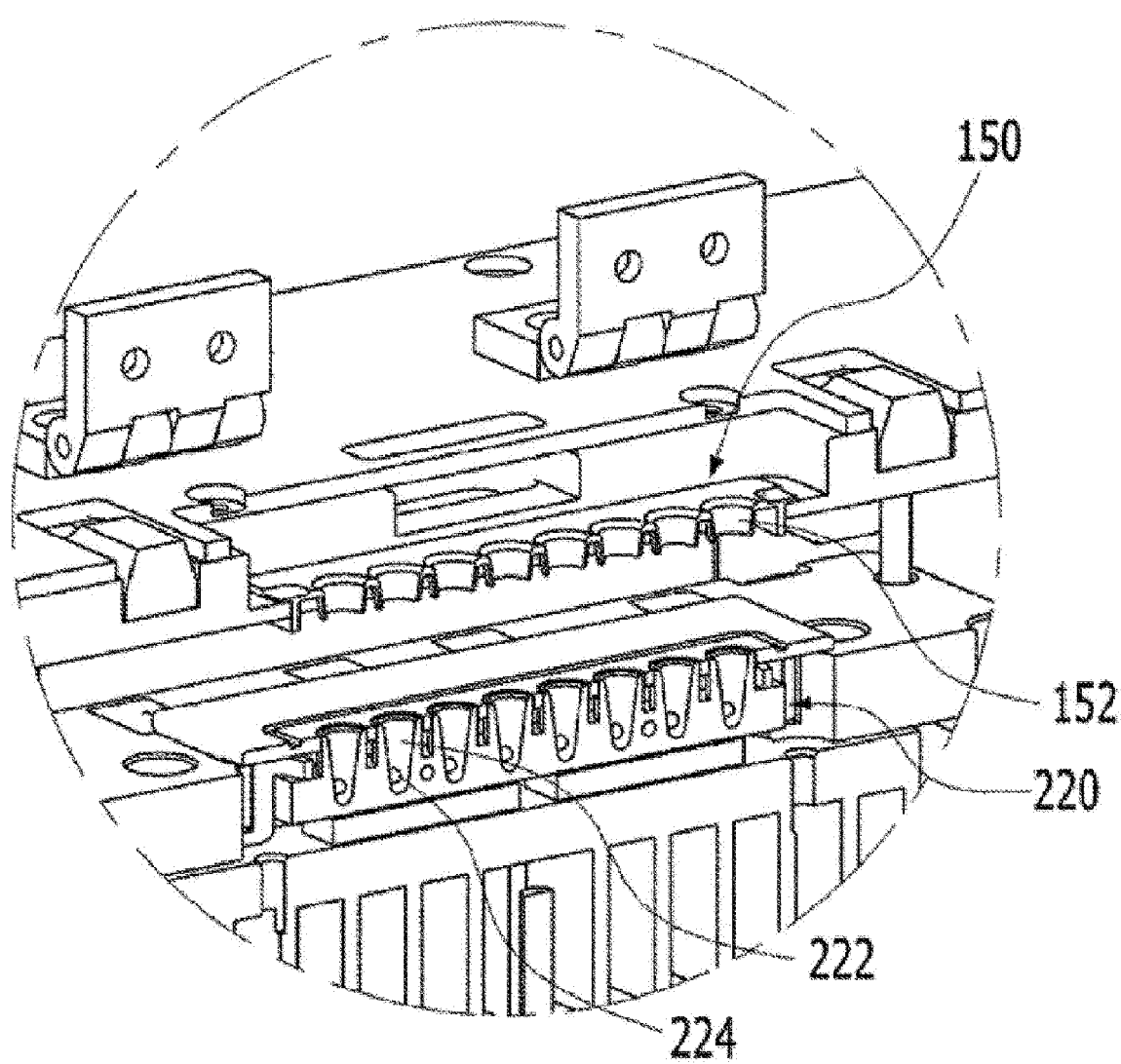
FIG. 13B is a view of portion R in FIG. 12 after removal of a tube as viewed from a different direction.
Figure 14:
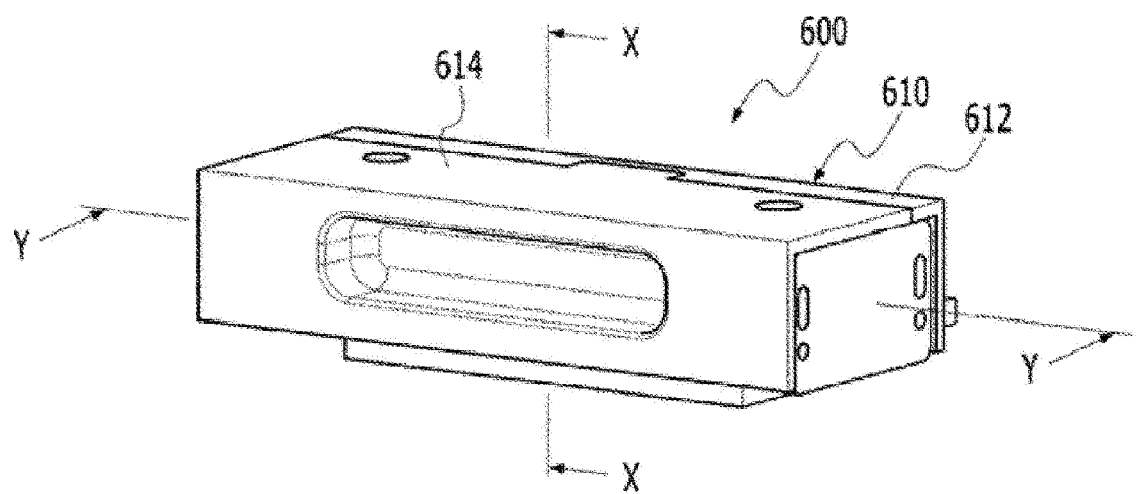
FIG. 14 is a view illustrating the cover module of the nucleic acid amplification apparatus according to the present invention.
Figure 15:
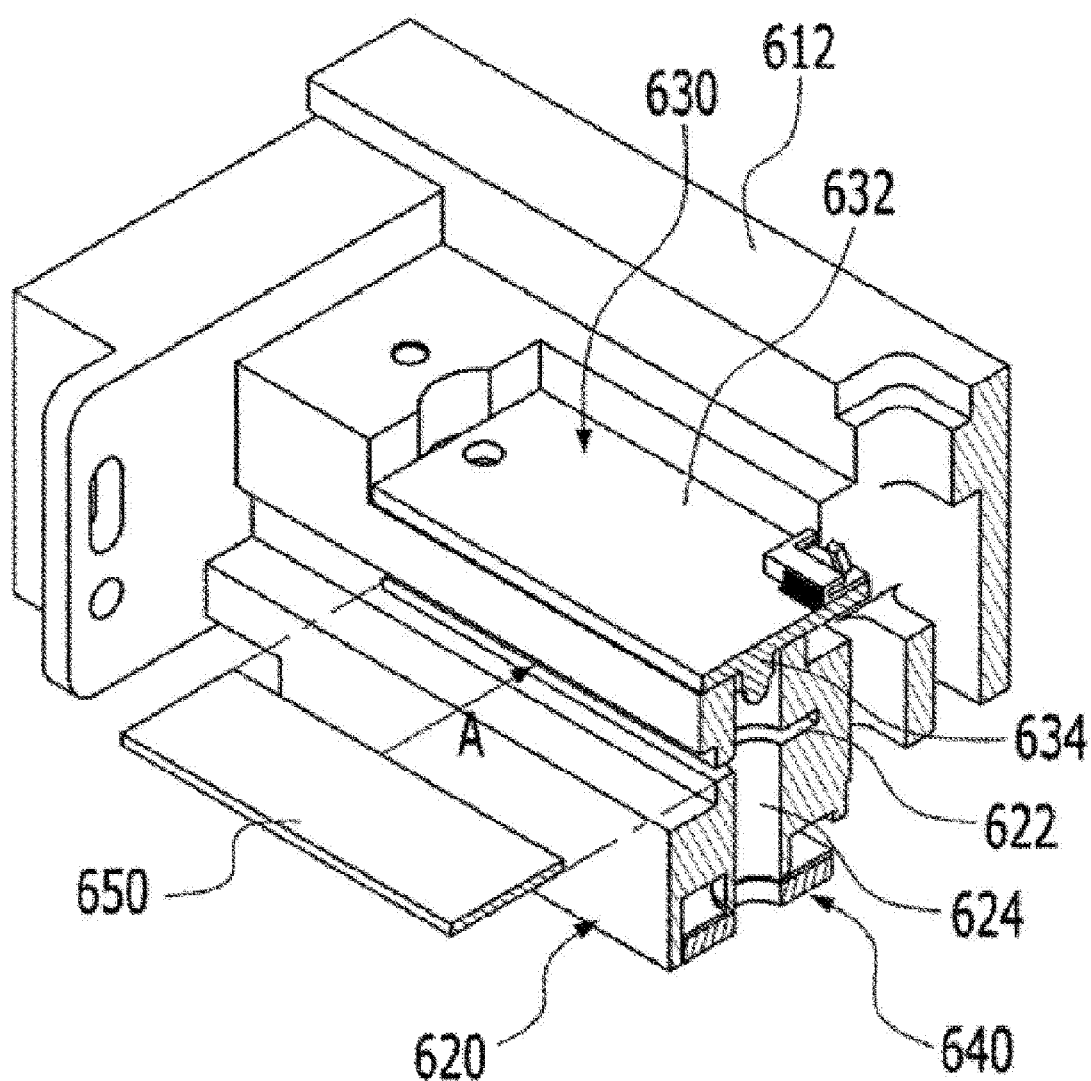
FIG. 15 is a view illustrating the cross section taken along line X-X in FIG. 14.

FIGS. 1 and 2 are views illustrating the external appearance of a nucleic acid amplification apparatus according to the present invention, FIG. 3 is a view illustrating the state in which a cover module 600 on a casing 100 is removed from the nucleic acid amplification apparatus according to the present invention, and FIG. 4 is an enlarged view of portion P in FIG. 3. FIGS. 5 and 6 are views illustrating the state in which a side plate of the casing 100 is removed from the nucleic acid amplification apparatus according to the present invention. In addition, FIG. 7 is a view illustrating the cross section taken along line X-X in FIG. 1, and FIG. 8 is an enlarged view of portion Q in FIG. 7. FIG. 9 is a view illustrating a heating block of the nucleic acid amplification apparatus according to the present invention, FIG. 10 is a view illustrating the positional relationship between the heating block and a sensing module of the nucleic acid amplification apparatus according to the present invention, and FIG. 11 is a view illustrating a blower nozzle of the nucleic acid amplification apparatus according to the present invention. FIG. 12 is a view illustrating the cross section taken along line Y-Y in FIG. 1, FIG. 13A is an enlarged view of portion R in FIG. 12, and FIG. 13B is a view of portion R in FIG. 12 after removal of a tube as viewed from a different direction.

The nucleic acid amplification apparatus according to the present invention is a nucleic acid amplification apparatus that controls the temperature of a reactant accommodated in a tube T, and includes the casing 100 defining the external appearance of the apparatus, the tube T being at a fixed position on at least a portion of the casing, a heating module 200 located below the tube T and configured to generate heat so as to heat the tube T, a sensing module 300 configured to sense light generated in the tube heated by the heating module 200, a drive module 400 configured to vertically move the heating module 200 so as to vary a distance between the tube T and the heating module 200, a cooling module 500 configured to cool the reactant accommodated in the tube T, the cover module 600 disposed on the casing 100 and capable of providing light to the tube T, and a control device 700 configured to control the operation of the entire apparatus.

The casing 100 may have a hexahedral shape, and may include a lower plate 110 forming a bottom surface, an upper plate 120 forming an upper surface, and a side plate 130 forming a side surface. A holder 150, the heating module 200, the sensing module 300, the drive module 400, the cooling module 500, and the control device 700, which will be described later, may be mounted inside the casing 100.

The upper plate 120 may have an introduction opening 122 formed in the vertical direction so that the holder 150 is exposed upward. The tube T may be mounted at a fixed position in the holder 150 exposed through the introduction opening 122. In addition, the cover module 600 may be pivotably connected to the upper plate 120 to open or close a mounting hole 154. The specific configuration of the cover module 600 will be described later.

The upper plate 120 and the cover module 600 may be connected to each other by a hinge 160. In addition, the upper plate 120 may be provided with a fastener 124, which fastens the cover module 600 to the upper plate 120, and may also be provided with a display device 140, which displays the operational state of the apparatus.

The holder 150 may be disposed inside the casing 100, and may be exposed upward through the introduction opening 122 formed in the casing 100.

The holder 150 includes a holding body 152 in the form of a block. The holding body 152 may be fixed at a position on at least a portion of the casing 100. In addition, the holding body 152 may be provided with the mounting hole 154 in the upper surface thereof. The mounting hole 154 may be vertically formed, or may be recessed downward. Thus, the tube T in which a sample is accommodated may be mounted at a fixed position in the mounting hole 154. A plurality of mounting holes 154 may be provided and may be arranged to form a line. For example, as illustrated in the drawings, eight mounting holes 154 may be arranged in a line.

When the mounting hole 154 is vertically formed and the tube T is mounted in the mounting hole 154, a lower portion of the tube T may protrude downward from the holder 150 to thereby be exposed. In addition, the plurality of mounting holes 154 may be arranged to form a predetermined number of lines in parallel.

In addition, a fixing jig 156 may be provided to fix the holding body 152 to the lower surface of the upper plate 120 of the casing 100.

In addition, the casing 100 may be provided with a signal input/output device 170, which is capable of receiving and transmitting an electric signal, and a power supply device 180, which is capable of supplying power.

The heating module 200 may be located below the holder 150 and is capable of heating the reactant accommodated in the tube T mounted in the holder 150.

The heating module 200 is a three-dimensional structure, which may be shifted by the drive module 400, which will be described later. The heating module 200 may include a heater 210, a heating block 220 disposed above the heater 210, a guide unit 230 disposed on a side of the heater 210, and an opening and closing block 240 disposed above the heater 210.

The heater 210 serves to generate heat to heat the reactant accommodated in the tube T. For example, the heater may be operated in response to an electric signal generated in the control device 700. The heater 210 may be controlled to generate heat at a correct temperature as desired by the user. The heater 210 may be configured to have, for example, a Peltier element, without limitation thereto.

FIG. 9 is a view illustrating the overall structure of the heating block 220. Referring to FIG. 9, the heating block 220 may include recesses 222 and light transmitting portions 224. The heating block 220 may be disposed above the heater 210. The heating block 220 is configured to receive heat generated by the heater 210 and transfer the heat to the tube T mounted in the holder 150 located thereabove. The heating block 220 may be formed of a material having high thermal conductivity.

The recesses 222 are formed in the top of the heating block 220. The recesses 222 are formed at positions corresponding to the positions of the mounting holes 154 formed in the holder 150. The multiple recesses 222 may be formed to form a predetermined number of lines in parallel. For example, as described above, when eight mounting holes 154 are formed and arranged in a line, eight recesses 222 may also be formed and arranged in a line. In addition, each recess 222 may have a shape corresponding to the lower portion of the tube T so that the lower portion of the tube T may be introduced into and come into close contact with the recess 222.

The light transmitting portions 224 are formed in at least one side of the respective recesses 222 and take the form of passages which penetrate the recesses in the lateral direction. For example, the light transmitting portions 224 may be formed at the rear of the recesses 222, and may be passages which penetrate a rear portion of the heating block 220 in the front-and-rear direction.

The guide unit 230 may be connected to the lateral side of the heater 210. The guide unit 230 may include a guide pipe 232, a guide beam 234, and an elastic spring 236.

The guide pipe 232 included in the heating module 200 has a guide hole vertically formed therein and is fixed to the lateral side of the heater 210.

The guide beam 234 of the heating module 200 vertically extends through the guide hole. For example, the guide beam 234 may have a lower end fixed to the lower plate 110 and an upper end fixed to the upper plate 120 or the fixing jig 156.

The elastic spring 236 is disposed between the guide pipe 232 and the upper plate 120 so that the guide beam 234 passes through the elastic spring 236. Thus, when the elastic spring 236 is compressed, the elastic spring 236 applies an elastic force downward to the guide pipe 232. In other words, the elastic spring 236 may apply an elastic force to maintain the guide pipe 232 at the lowered position thereof. In addition, the elastic spring 236 prevents strong collision between the heating block 220 and the tube T when the heater 210 and the heating block 220 move upward, and may bring the heating block 220 and the tube T into close contact with each other.

The opening and closing block 240 includes an upright shield having a predetermined height and a predetermined thickness. The opening and closing block 240 is disposed above the heater 210 at the lateral side of the heating block 220. The opening and closing block 240 may be vertically erected to have a predetermined height and may be located between a blower nozzle 520 and the heating block 220.

The sensing module 300 may include a module housing 310, a light capturing unit 320, and an emission filter 330. The sensing module 300 may be disposed on the heater 210 of the heating module 200 and may be shifted along with the heating module 200.

The module housing 310 may include a module cover 312 and a module base 314. The module housing 310 may be configured to accommodate the light capturing unit 320 and the emission filter 330 therein.

The heating block 220 may also be mounted inside the module housing 310, and the module cover 312 may have an upwardly open space so as to upwardly expose the recesses 222 in the heating block 220. In addition, the module base 314 includes a mounting wall 316 to which the heating block 220 is coupled, and the light capturing unit 320 and the emission filter 330 are also mounted to the mounting wall 316. A through-hole 318 may be formed in the mounting wall 316 at a position corresponding to the position of each light transmitting portion 224 in the heating block 220 so as to communicate with the light transmitting portion 224.

The light capturing unit 320 may be configured in such a manner that sensors 324 are mounted on a printed circuit board (PCB) 322. The sensors 324 may be, for example, photodiodes and the number and arrangement of sensors 324 may correspond to the number and arrangement of light transmitting portions 224. That is, eight light transmitting portions 224 may be formed to correspond to the number of recesses 222 in the heating block 220, and eight sensors 324 may be provided to correspond to the respective light transmitting portions 224. For example, as illustrated in FIG. 10, the PCB 322 may be erected behind the heating block 220, and the sensors 324 and the light transmitting portions 224 may face each other.

The emission filter 330 may be disposed between the light capturing unit 320 and the heating block 220. The emission filter 330 is a band-pass filter that passes only the light of the wavelength generated by a fluorescent material of the tube due to incident light. Thus, the light generated in the tube may pass through the light transmitting portion 224 and the emission filter 330 behind the heating block 220 to thereby be introduced into the sensor 324 of the light capturing unit 320.

The drive module 400 serves to shift the heating module 200 and the sensing module 300.

The drive module 400 is located below the heating module 200. The drive module 400 may include a motor 410 and a motor shaft 420, for example. The motor shaft 420 is connected to a lower portion of the heating module 200. When the motor 410 is operated, the motor shaft 420 may be moved upward to shift the heating module 200 upward. Needless to say, the present invention is not limited thereto, and the drive module 400 may have any other configuration as long as it may shift the heating module 200 and the sensing module 300.

With the operation of the drive module 400, the heating module 200 and the sensing module 300 may reciprocate between the raised position and the lowered position thereof. For example, when the drive module 400 moves upward, the heating module 200 and the sensing module 300 may be moved to the raised position. When the drive module 400 moves downward, the heating module 200 and the sensing module 300 may be moved to the lowered position.

The cooling module 500 includes a blower fan 510 and the blower nozzle 520.

The blower fan 510 serves to generate an airflow to cool the tube T. The blower fan 510 may include a propeller and the motor 410, although not illustrated.

The blower nozzle 520 serves to transmit the airflow generated by the blower fan 510 to the tube T mounted in the holder 150. The blower nozzle 520 is configured to have a predetermined inner space penetrating in opposite directions. One side of the space functions as an inlet 522 and is disposed adjacent to the blower fan 510, and the other side of the space functions as an outlet 524 and is disposed adjacent to the holder 150.

As illustrated in FIG. 11, the outlet 524 may be shaped so as to be horizontally wider and vertically narrower than the inlet 522. Thus, the blower nozzle 520 may have a funnel shape with a narrow inlet and a wide outlet when viewed from above, and may have the shape of the number "6" with a wide inlet and a narrow outlet when viewed from the lateral side.

The outlet 524 of the blower nozzle 520 may be located parallel to the arrangement of a plurality of tubes T mounted in the holder 150 and may be configured to uniformly provide cooling air to the plurality of tubes T mounted in the holder 150.

That is, referring to FIG. 13A, the width direction of the outlet 524 may be parallel to the line along which the arrangement of the mounting holes 154 is formed.

The cover module 600 is a cover that is pivotably connected to the upper plate 120 of the casing 100 via the hinge 160, as described above. Hereinafter, the cover module 600 will be described with reference to FIGS. 14 to 17. The cover module 600 may be disposed on the holder 150, and may include a cover housing 610, a cover base 620, a light emitting unit 630, an excitation filter 650, and a tube cap heating element 640.

The entire cover housing 610 may have a rectangular parallelepiped shape, and may include a housing portion 612 having a predetermined space therein and an opening and closing cover 614 connected to the housing portion 612 so as to be opened and closed.

The cover base 620 is mounted inside the cover housing 610. When the opening and closing cover 614 is opened, at least a portion of the cover base 620 is exposed. The cover base 620 has a filter insertion slot 622 and light passages 624. The filter insertion slot 622 is formed in the front surface of the cover base 620, and has a predetermined depth in the rearward direction and a predetermined width in the lateral direction. The light passages 624 are formed so as to extend vertically through the filter insertion slot 622.

The light emitting unit 630 includes a PCB 632 and a plurality of light sources 634 mounted on the lower surface of the PCB 632. The PCB 632 is mounted on the upper surface of the cover base 620 as illustrated by the arrow B in FIG. 16, and each of the light sources 634 is located at a position corresponding to the position of each light passage 624. Thus, the number of light sources 634 and the number of light passages 624 may be the same.

The arrangement of the light passages 624 and the light sources 634 may be the same as the arrangement of the recesses 222 in the heating block 220. That is, eight light sources 634 and eight light passages 624 may be arranged in a line above the recesses 222 to correspond to the arrangement in which eight recesses 222 are arranged in a line.

The excitation filter 650 is an optical band-pass filter having a predetermined thickness and a predetermined area. The excitation filter 650 passes only light of a specific wavelength, suitable for a fluorescent material used for a reaction occurring in the apparatus, of broadband light emitted from the light sources 634 of the light emitting unit 630 and causes the light to be introduced into the reactant in the tube. The filter may be inserted into the filter insertion slot 622 formed in the cover base 620 as illustrated by the arrow A in FIGS. 15 and 16. When the excitation filter 650 is inserted into the filter insertion slot 622, the excitation filter 650 crosses at least a portion of the light passage 624. Alternatively, the opening and closing cover 614 may be opened to remove and replace the excitation filter 650.

Figure 16:
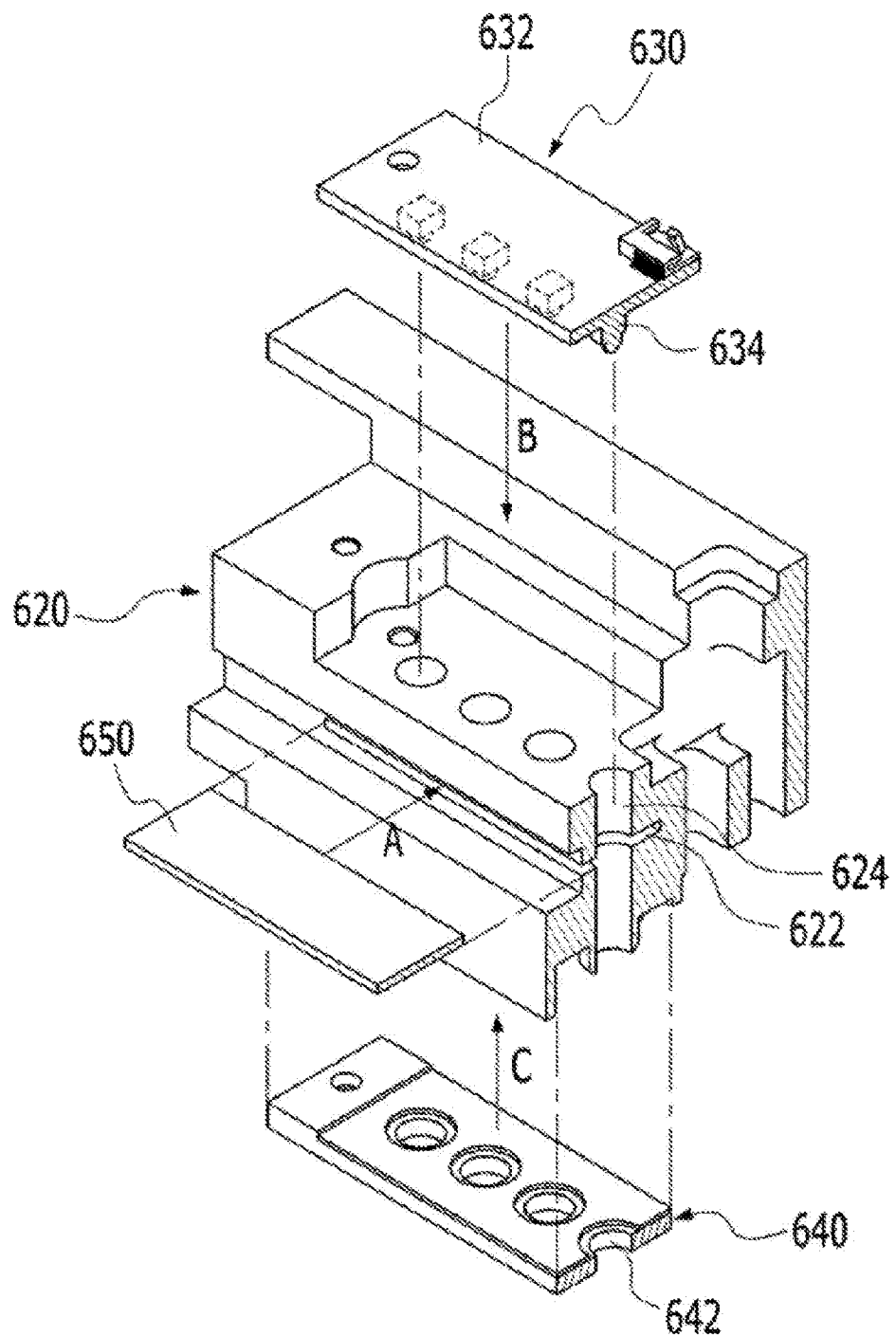
FIG. 16 is a view illustrating the coupling structure of the cover module of the nucleic acid amplification apparatus according to the present invention.
Figure 17:
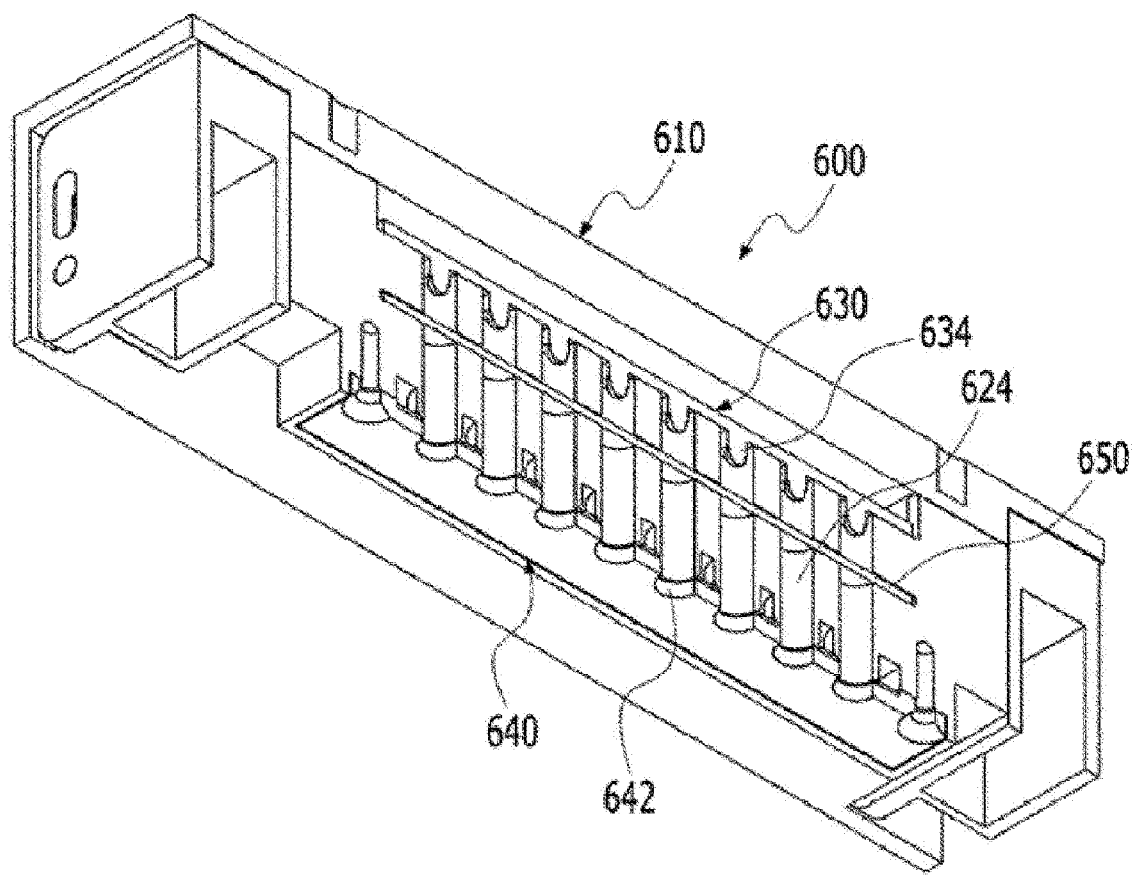
FIG. 17 is a view illustrating the cross section taken along line Y-Y in FIG. 14.

The tube cap heating element 640 is mounted on the lower surface of the cover base 620 as illustrated by the arrow C in FIG. 16 and is capable of radiating heat. The tube cap heating element 640 may be formed with a plurality of through-holes 642, which are vertically formed, and the plurality of through-holes 642 may be arranged to correspond to the arrangement of the light passages 624 so that the light emitted from the light emitting unit 630 passes through the through-holes and is introduced into the tube.

The tube cap heating element 640 serves to heat a cap of the tube in order to prevent water vapor evaporated due to a high temperature reaction from condensing on the lower surface of the cap and forming droplets, thereby minimizing a change in the volume of a sample and maintaining a constant amount of light irradiated through the cap from a light source above the tube for the measurement of fluorescence.

The control device 700 may be a CPU capable of controlling the operation of the heating module 200, the sensing module 300, the drive module 400, and the cooling module 500. The control device 700 may control the operation of the heating module 200, the sensing module 300, the drive module 400, and the cooling module 500 upon receiving an external signal, and may output the operational state.

Figure 19:
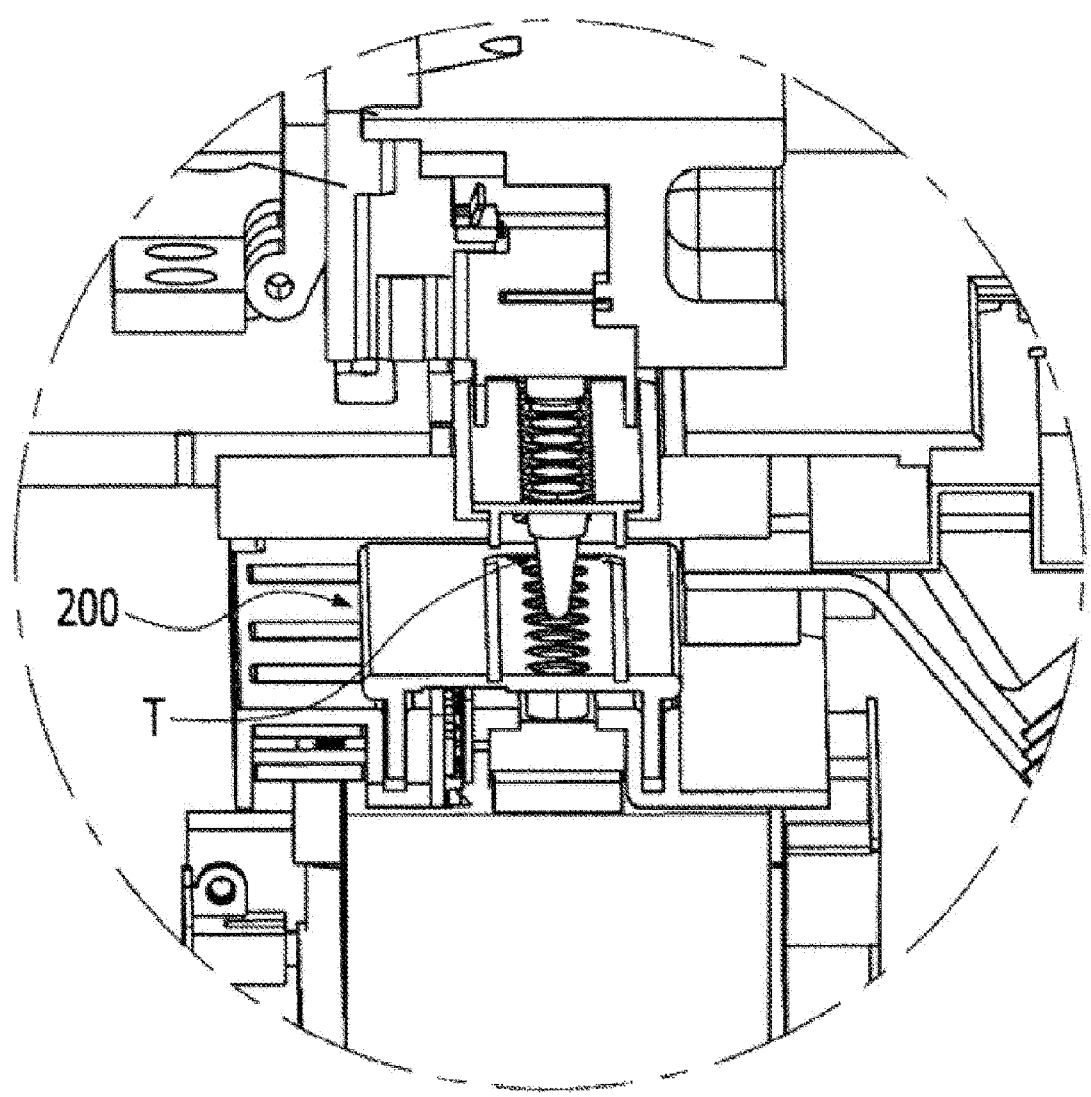
FIG. 19 is a view illustrating the state in which a heating module of the nucleic acid amplification apparatus according to the present invention is located at the lowered position thereof.
Figure 20:
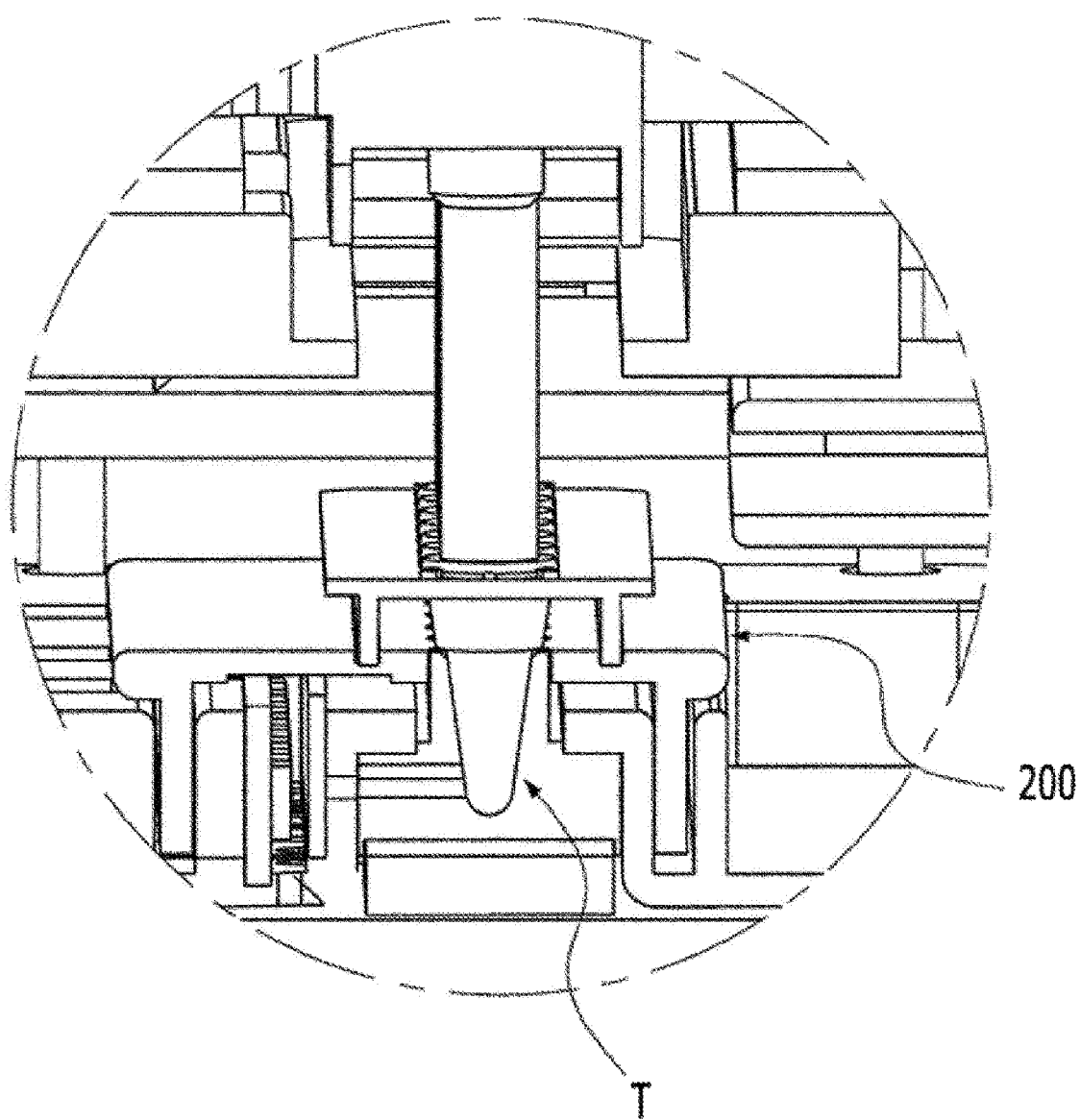
FIG. 20 is a view illustrating the state in which the heating module of the nucleic acid amplification apparatus according to the present invention is located at the raised position thereof.
Figure 21:
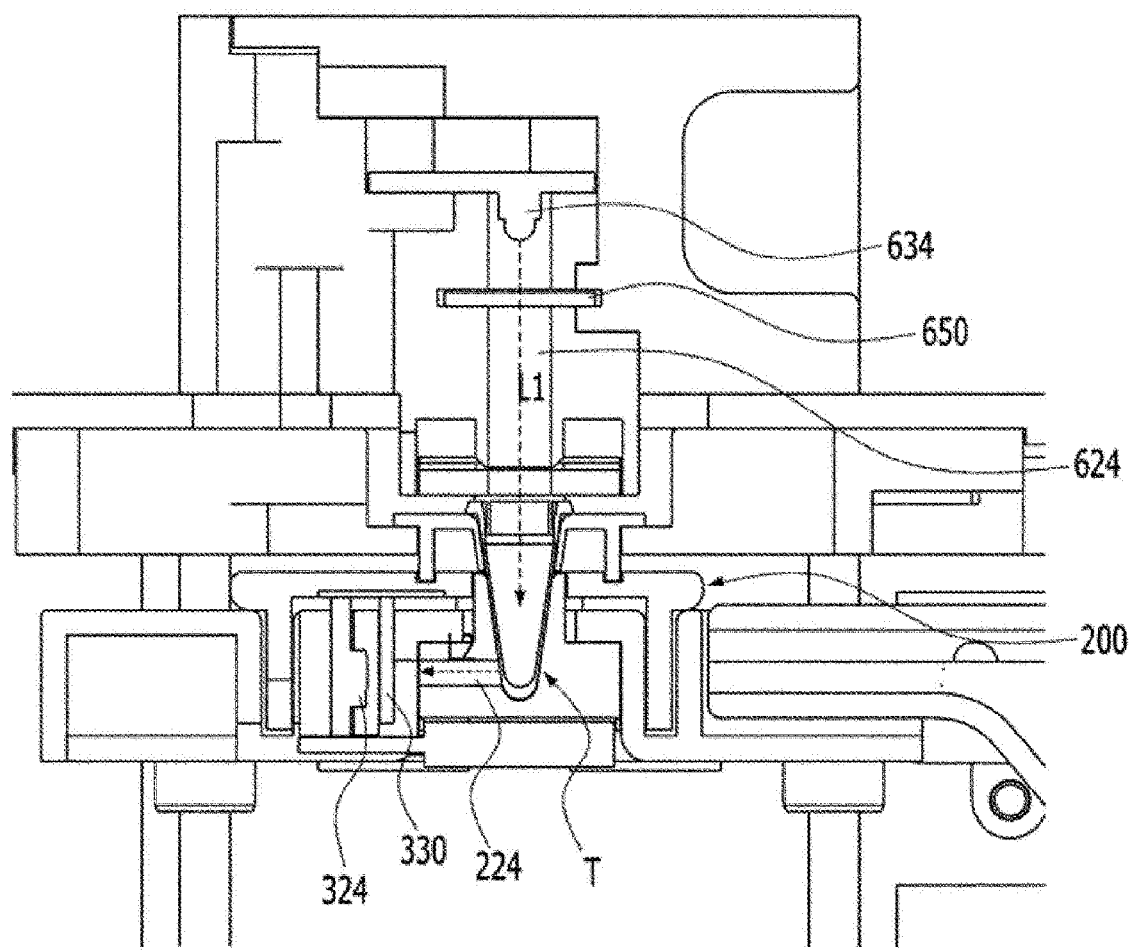
FIG. 21 is a view illustrating the path of light generated in the cover module of the nucleic acid amplification apparatus according to the present invention.

Hereinafter, the operation of the nucleic acid amplification apparatus according to the present invention will be described. FIG. 19 is a view illustrating the state in which the heating module 200 of the nucleic acid amplification apparatus according to the present invention is located at the lowered position thereof. FIG. 20 is a view illustrating the state in which the heating module 200 of the nucleic acid amplification apparatus according to the present invention is located at the raised position thereof. In addition, FIG. 21 is a view illustrating the path of light generated in the cover module 600 of the nucleic acid amplification apparatus according to the present invention.

First, the tube T in which a reactant is accommodated is mounted in the holder 150. At this time, the tube T may be mounted by opening the cover module 600 on the casing 100, introducing the tube T into the mounting hole 154 in the holder 150 to mount the tube T, and thereafter, closing the cover module 600.

Figure 18:
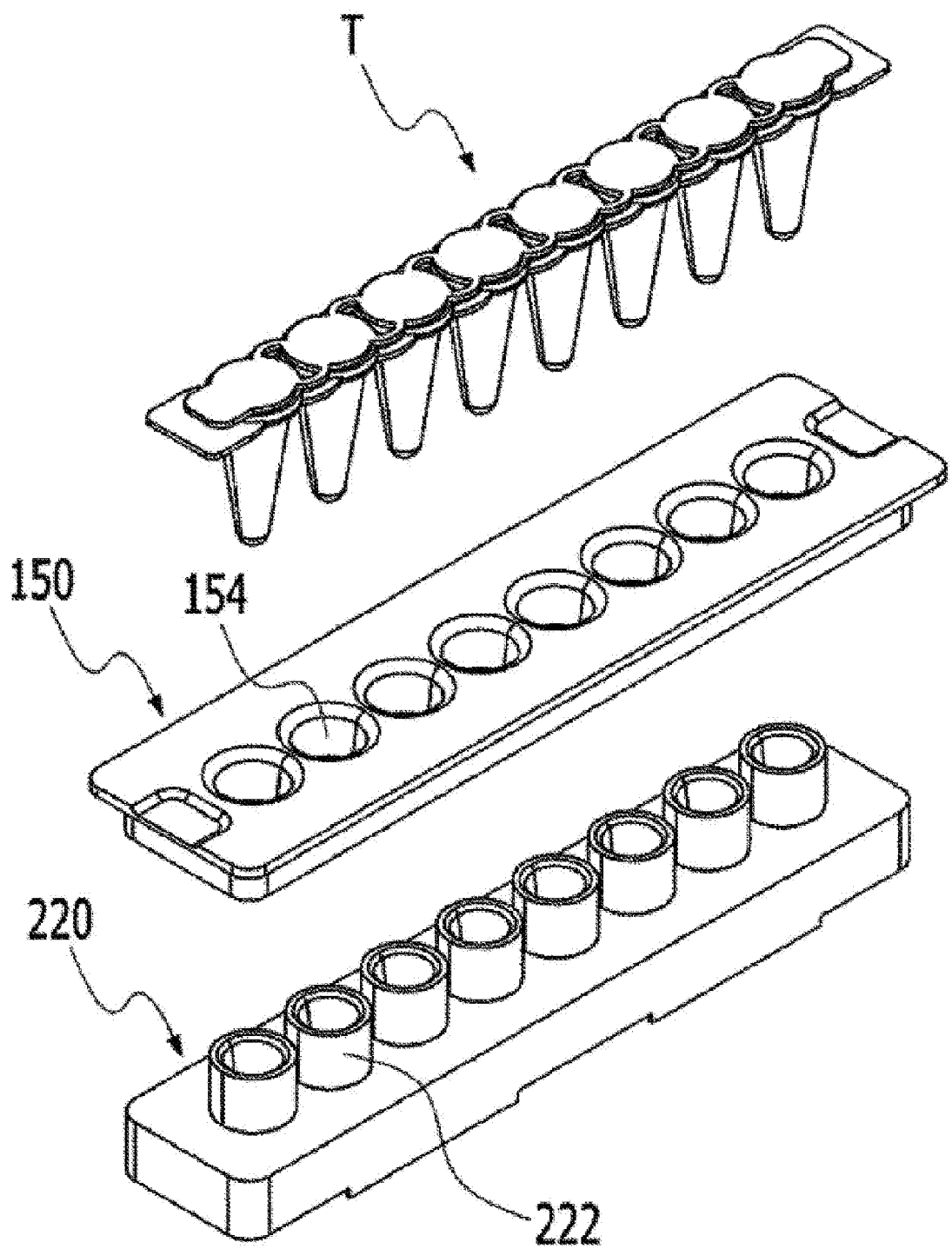
FIG. 18 is a view illustrating the relationship between a tube, a holder, and the heating block of the nucleic acid amplification apparatus according to the present invention.

At this time, as illustrated in FIG. 18, the tube T is first accommodated in the mounting hole 154 in the holder 150. Since the drive module 400 is not yet operated, the heating module 200 and the sensing module 300 are located at the lowered position thereof and the heating block 220 is spaced apart from the holder 150.

The heating module 200, the sensing module 300, the drive module 400, the cooling module 500, and the cover module 600 may be operated when an operation signal is generated by the control device 700. Alternatively, respective operations may be performed at the same time or may be performed with a time difference, and the implementation manner thereof is not limited.

When the operation signal is transmitted to the heating module 200, the heater 210 may be operated to generate heat. In addition, when an operation signal is transmitted to the drive module 400, the motor 410 is operated to raise the heating module 200. Thereby, the heating module 200 is moved to the raised position thereof as illustrated in FIG. 20.

When the heating module 200 is raised by the drive module 400 and the heating block 220 of the heating module 200 approaches the holder 150, the reactant in the tube T mounted in the holder 150 is heated. At this time, the surface of the recess 222 formed in the heating block 220 and the lower surface of the tube T may be in contact with each other to enable rapid heat transfer.

At this time, since it is not necessary to cool the tube T when the heating module 200 is raised, the blower fan 510 of the cooling module 500 may be stopped.

Alternatively, according to one example, when the heating module 200 is raised, the opening and closing block 240 of the heating module 200 is raised. The raised opening and closing block 240 may close the outlet 524 in the blower nozzle 520 of the cooling module 500 so as to prevent cooling air generated by the cooling module 500 from being transmitted to the tube T.

At this time, as illustrated in FIG. 21, light is generated in the light source 634 provided in the cover module 600. The light generated in the light source 634 passes through the excitation filter 650 to have an appropriate wavelength, and then passes through the light passage 624 and the through-hole 642 to thereby be introduced into the tube T. When the light is incident on the reactant in the tube T, a fluorescence signal is generated due to amplification of a nucleic acid in the tube. The fluorescence signal is transmitted through the light transmitting portion 224 of the heating block 220 to pass through the emission filter 330, and is then introduced into the sensor 324. In this way, a reaction of the reactant in the tube may be detected in real time.

When the heating module 200 is maintained at the raised position for a predetermined time and a designated heating time elapses, the control device 700 may generate a signal to reversely operate the motor 410 of the drive module 400.

When the motor 410 of the drive module 400 is reversely operated, the heating module 200 is lowered. As the heating module 200 is lowered, the tube T and the heating block 220 are spaced apart from each other and the heating of the tube T by the heating block 220 is stopped. Here, the term "stop" is not limited to the meaning that heat transfer is completely excluded.

When the heating module 200 is lowered, the blower fan 510 is operated to cool the tube T. Alternatively, according to one example, when the opening and closing block 240 provided in the heating module 200 is lowered, the outlet 524 in the blower nozzle 520 is opened so that the tube T mounted in the holder 150 may be cooled by the cooling airflow generated by the blower fan 510.

When the heating module 200 is maintained at the lowered position for a predetermined time and a designated cooling time elapses, the control device 700 generates a signal to operate the drive module 400 again so that the heating block 220 is raised to heat the reactant in the tube T mounted in the holder 150. Then, when a heating time elapses, the heating block 220 is lowered as described above and the tube is exposed to the air so as to be cooled. This process is repeated a predetermined number of times.

According to the present invention, the temperature of the reactant may be rapidly controlled. That is, the tube T in which the reactant is accommodated may be brought into contact with the heating block 220 of the heating module 200 so as to be rapidly heated. When the heating is sufficiently performed, the heating module 200 or the holder is moved to open the blower nozzle 520 so that the reactant may be rapidly cooled by the cooling air generated in the blower fan 510.

In addition, when the operation of the heating module 200 or the holder 150 is set according to user intention, the heating time and the cooling time of the reactant may be controlled so that the reactant reaches any of various target temperatures and a target temperature range may be maintained. For example, when the operation cycle of the heating module 200 is changed or when the time during which the heating module 200 is maintained at the raised position thereof or the time during which the heating module 200 is maintained at the lowered position are set differently, the heating time and cooling time of the reactant may be set differently so that the temperature of the reactant may be easily controlled and selected as desired by the user.

In addition, the heating and cooling of the reactant may be achieved with a very simple operation. That is, when the heating block 220 and the opening and closing block 240 provided in the heating module 200 are raised and lowered together at the time of heating, the heating block 220 may approach the tube T to perform rapid heating and the opening and closing block 240 may close the blower nozzle 520 to prevent cooling by the cooling airflow. In addition, at the time of cooling, the heating block 220 is spaced apart from the tube T to stop the heating, and the opening and closing block 240 is spaced apart from the blower nozzle 520 to open the blower nozzle 520 so that rapid cooling by the cooling airflow is achieved. In this way, the heating and cooling of the reactant may be appropriately performed simply by an operation signal for the drive module 400 which moves the heating module 200 without requiring the input of a separate cooling operation signal.

In addition, in the heating process, the light generated in the light source 634 of the cover module 600 is incident on the reactant in the tube T and the light generated in the reactant is transmitted to and sensed by the sensor 324, whereby the reaction result of the reactant may be detected in real time.

Accordingly, a polymerase chain reaction (PCR), which is a typical chemical and biochemical reaction requiring temperature control may be performed rapidly and accurately.

In another aspect, the present invention also relates to a method of controlling the temperature of a reaction solution in a nucleic acid amplification reaction.

The method according to the present invention may be performed using the apparatus as described above or an apparatus exemplified in FIGS. 22A and 22B.

In the method according to the present invention, heating and cooling are performed using separate devices in such a manner that a reaction vessel in which a reaction solution is accommodated is moved between a heating block maintained at a high temperature and an airflow generated by a blower fan so as to be repeatedly exposed to the heating block and the airflow, which results in temperature control.

The method according to the present invention may be used for temperature control in a technology of amplifying a target specific nucleic acid using a periodic temperature change, for example, a polymerase chain reaction (PCR). In such a PCR, generally, three reaction steps constitute one cycle, and the cycle is repeated at least 2 times, at least 2 to 50 times, at least 2 to 40 times, or at least 2 to 30 times, without limitation thereto. The PCR is a process of amplifying a small amount of target to enable detection thereof, and may be performed in various ways according to the amount of a target present in a sample, the degree of impurities contained in the sample, the type of a detection method, the purpose of detection, the type of enzymes, and PCR conditions, and those skilled in the art will be able to determine the number of cycles suitable for such conditions.

To explain, in a first denaturation step, a double-stranded nucleic acid is divided into single strands at a temperature of 90° C. or higher. A second annealing step usually takes place at 55° C. to 60° C., in which two types of primers are bound to complementary portions of the respective nucleic acid strands which have been separated into single strands in the denaturation step. In a third extension step, extension in which a DNA polymerase synthesizes a DNA using a single strand as a template and using base monomers (dNTPs) from a primer. At this time, the temperature usually ranges from 65° C. to 75° C. That is, the PCR usually proceeds within a temperature range of 55° C. to 95° C. while repeating a temperature change for heating and cooling, and the target nucleic acid is amplified by repeating this heating and cooling process 25 to 40 times. In the PCR, the annealing and extension steps may be performed in one step according to a specific temperature, in which case one cycle consists of two steps including a denaturation step and an annealing and extension step. The present invention may be applied to both the methods described above.

Figure 31:
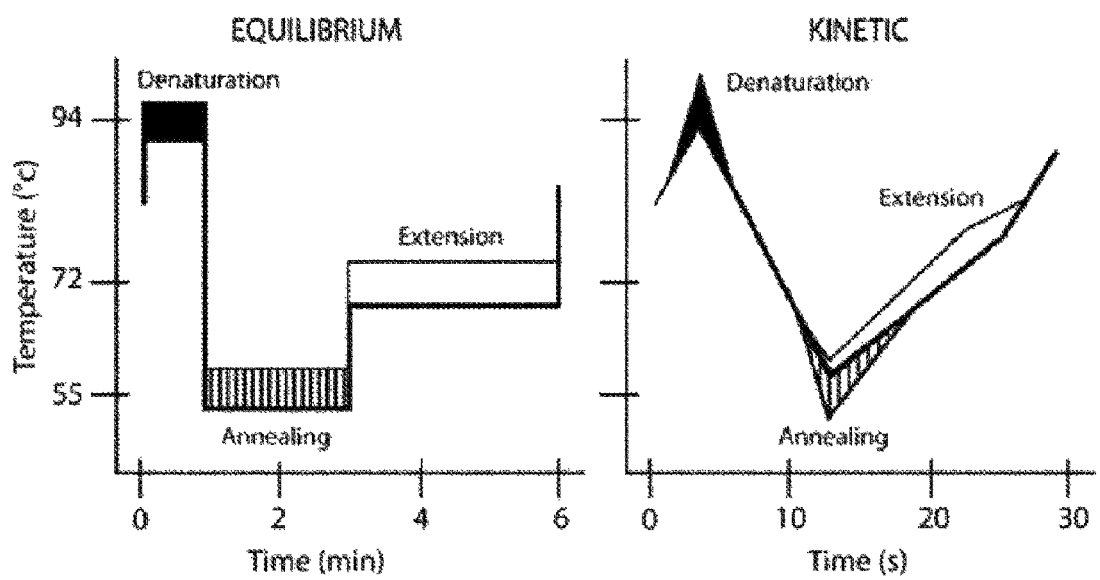
FIG. 31 is a graph illustrating two conditions for performing a PCR (see: "The PCR Revolution: Basic technologies and applications" edited by Stephen A. Bustin, "Chapter 4: Rapid polymerase chain reaction and melting analysis" by Carl T. Wittwer, Randy P. Rasmussen, and Kirk M. Ririe).

The PCR method as described above may be divided into two manners as described in FIG. 31 in terms of equilibrium and kinetic power paradigm according to a temperature state. The former method is mainly used in the past, in which each step is performed at a specific temperature for a predetermined time, and a temperature change period due to the transition from one step to the next step is not considered in a reaction. On the other hand, in the latter method, each step is not maintained at a specific temperature for a predetermined time, but each step proceeds at a continuously changing temperature, that is, a reaction of each step occurs over a specific temperature range. Thus, the reaction rate of each step of the PCR such as annealing, extension, and denaturation depends on the temperature, and one or more reactions (denaturation, annealing, and extension) may occur at the same time at a specific temperature for a temperature change period.

The method according to the present invention is particularly optimized for the PCR in the latter manner. Such a method may exhibit somewhat low sensitivity or specificity as compared to conventional methods, but may be very conveniently used for applications in which large quantities of samples need to be screened quickly.

Accordingly, in one aspect, the present invention relates to a method of controlling the temperature of a nucleic acid amplification reaction including a denaturation step performed at a first temperature and an annealing and extension reaction step performed at a second temperature, these steps being repeated multiple times.

In one embodiment, the method includes a first step of heating a vessel used for a nucleic acid amplification reaction to a first temperature by bringing the vessel into contact with a heating block consistently maintained at the first temperature for a predetermined time, and a second step of cooling the vessel to a second temperature by separating the heating block from the vessel by a predetermined distance so that the separated vessel is exposed to an artificial airflow for a predetermined time, and the first and second steps are repeated multiple times with respect to the vessel cooled to the second temperature.

Alternatively, in another aspect, the present invention relates to a method of controlling the temperature of a PCR in three steps, i.e., a denaturation step performed at a first temperature, an annealing step performed at a second-first temperature, and an extension step performed at a second-second temperature, which constitute one cycle.

In one embodiment, the method includes a first step of heating a vessel used for a nucleic acid amplification reaction to a first temperature by bringing the vessel into contact with a heating block consistently maintained at the first temperature for a predetermined time, a second step of cooling the vessel to a second-first temperature by separating the vessel from the heating block by a predetermined distance so that the separated vessel is exposed to an airflow for a predetermined time, and a third step of cooling the exposed vessel to a third temperature by exposing the vessel to an airflow for a predetermined time.

Recently, large quantities of samples are used for the purpose of screening, and a rapid reaction is essential for this. In the PCR, however, temperature control during the heating and cooling process is a key factor in achieving a rapid reaction.

In the method according to the present invention, in a first step, a reaction vessel in which a reaction solution is accommodated comes into contact with a heating block, maintained at a specific temperature for a predetermined time, so as to be heated for a predetermined time until the reaction solution reaches a target denaturation temperature. Subsequently, in a second step, the vessel is separated from the heating block and is moved in a predetermined direction so as to be exposed to an artificial airflow generated by a blower fan for a predetermined time until the reaction solution is cooled to reach a target cooling temperature. At this time, the temperature of the reaction solution may be controlled to reach various target temperatures by controlling the contact time with the heating block or the contact time with the airflow generated by the blower fan. By repeating this process, the temperature of the reaction solution may be controlled so as to repeatedly reach specific temperature ranges.

In one embodiment, the artificial airflow generated by the blower fan, i.e., the wind, is at room temperature. The room temperature may vary somewhat for each environment, but the velocity of the airflow may be controlled via the RPM of the fan that generates the airflow using an outside temperature measurement thermometer attached to the apparatus. In addition, when used in a room, considering the temperature condition of the PCR, there is substantially no difference in cooling time when the temperature of the airflow is 20° C., 30° C., or 35° C. within the PCR temperature range of 55° C. to 65° C. On the other hand, the velocity of the airflow may affect the cooling time.

The time required to cool the reaction solution, heated to 98° C. for nucleic acid denaturation, to a general annealing or extension temperature of 65° C., i.e., a predetermined time for the exposure of the reaction solution to the artificial airflow, is related to the velocity of the airflow blown toward the reaction vessel. In one embodiment, the cooling time may be determined by the following equation: $t=4+2\times e^{-(v-7.4)/6.2}$.

Figure 32:
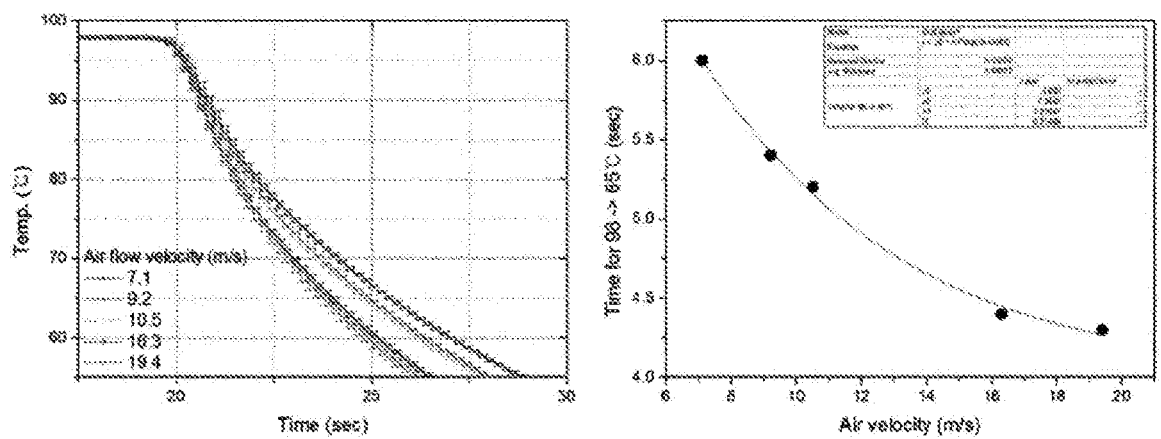
FIG. 32 is a graph illustrating the relationship between the time t required when the temperature is lowered from 98° C. to 65° C. in a PCR and the velocity v of cooling air.

For example, when a standard PCR tube for a general PCR is used as a reaction vessel and a reaction solution of 20 µl is used, the time t required for cooling the reaction solution from 98° C. to 65° C. as illustrated in FIG. 32 may be determined from the above equation based on the velocity v of cooling airflow.

In the present invention, the temperature is based on the reaction solution or a reactant accommodated in the reaction vessel. However, due to the characteristics of the PCR by the method according to the present invention, it can be said that there is no difference in the temperature between the vessel and the solution in consideration of the material of a general PCR tube which shows excellent heat transfer and has a very small volume of about 1 µl to 50 µl. Thus, unless otherwise specified herein, the temperature of the reaction vessel refers to the temperature of the reactant or the reaction solution.

Figure 22A:
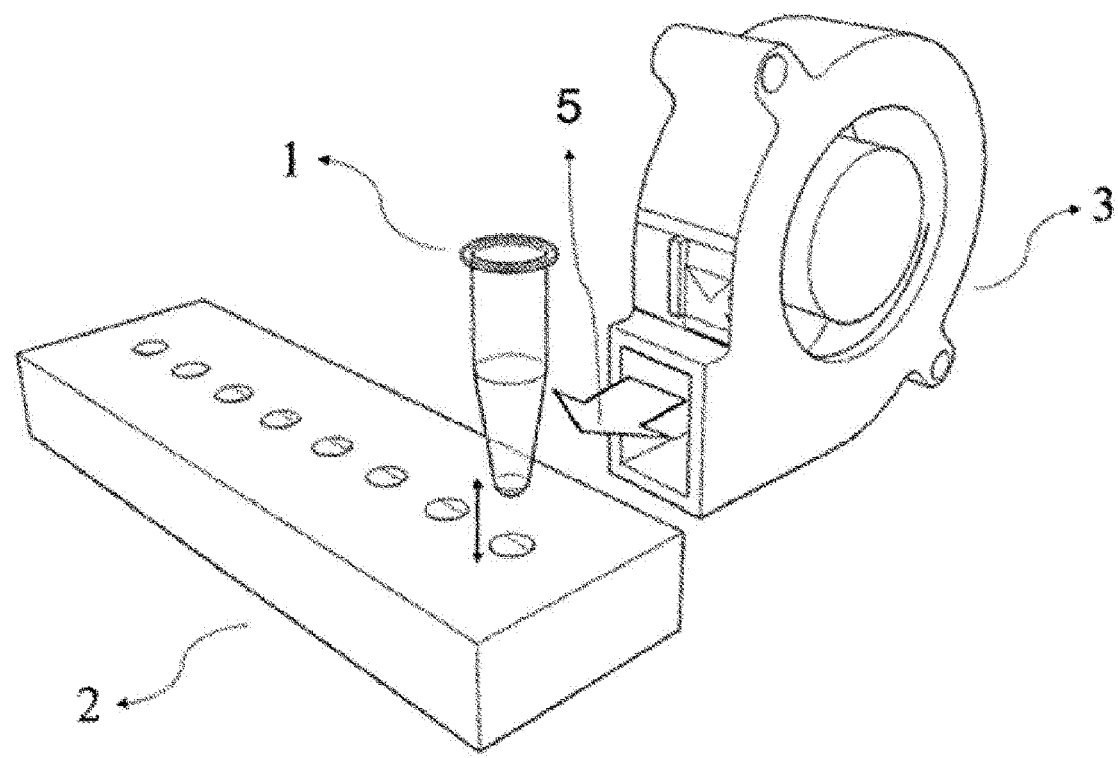
FIGS. 22A and 22B are views diagrammatically illustrating the external appearance of an exemplary apparatus which may be used in a method according to the present invention, the apparatus according to an embodiment including a reaction vessel 1, a heating block 2, and a blower fan 3, and the reaction vessel 1 in which a reaction solution is accommodated being moved so as to be brought into contact with each of the heating block 2 and an airflow 5 generated from the blower fan 3.
Figure 22B:
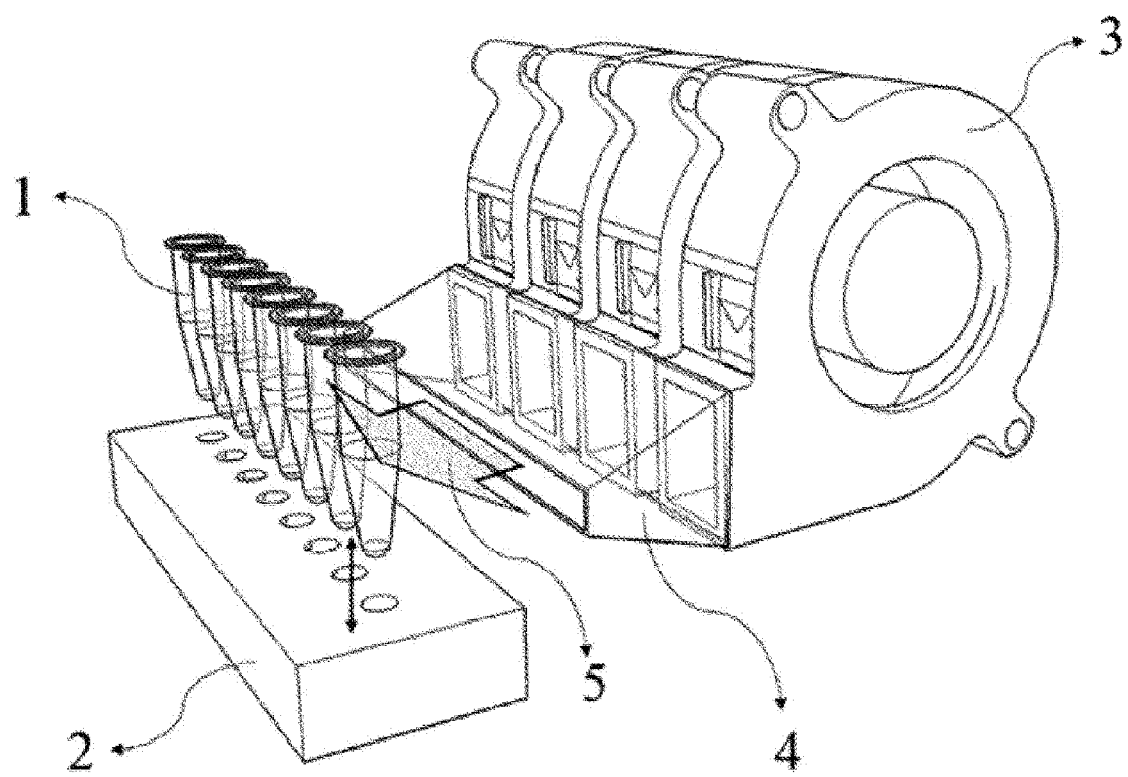

In one embodiment, the method according to the present invention may be performed using the apparatus described above as illustrated in FIGS. 1 to 21 or the apparatus as illustrated in FIGS. 22A and 22B. Specifically, the apparatus in which a blower fan 3, which is configured to blow an airflow 4, is located above a heating block 2, which has a hole formed in the shape of a reaction vessel so that a bottom portion of the reaction vessel 1 may completely come into contact with the heating block and which is formed of a metal material so as to be heated to and maintained at a high temperature may be used. In a first step, the reaction vessel 1 in which a reaction solution is accommodated is brought into contact with the heating block 2 so as to be heated, and then is moved upward so as to be exposed to the airflow 4 generated by the blower fan 3 to thereby be cooled. In this case, heating and cooling of a reactant may be achieved with very simple operations. That is, at the time of heating, the reaction vessel is mounted to the heating block to enable rapid heating and an opening and closing block closes a blower nozzle to prevent cooling by the cooling airflow. Alternatively, the airflow may be continuously generated if necessary. In addition, at the time of cooling, the heating block is spaced apart from the vessel to stop the heating, and the opening and closing block is spaced apart from the blower nozzle to open the blower nozzle, so that rapid cooling by the cooling airflow may be achieved.

A first step of the method according to the present invention includes heating the reactant in the reaction vessel to a first temperature.

In the method according to the present invention, the reactant is accommodated in the reaction vessel, and the reaction vessel may differ according to the specific configuration of the apparatus which implements the method according to the present invention, but may use, for example, a tube having a capacity of 100 µl or 200 µl, a capillary tube, a microfluidic channel, or a thin film chamber, which is generally used in a PCR, without limitation thereto.

The first temperature in the first step of the method according to the present invention means a temperature sufficient to separate a double-stranded DNA into single strands in a nucleic acid amplification reaction. The first temperature may be determined by various factors such as the composition of a base constituting a DNA, e.g., a G/C composition ratio, the total length, or the concentration of salt contained in a buffer, and those skilled in the art will be able to select an appropriate temperature in consideration of reaction conditions, for example. For example, the first temperature may be not lower than 90° C. or may be about 95° C., without limitation thereto.

The heating of the reactant in the first step of the process according to the present invention may be performed using the heating block. In particular, the heating block is fixed at the first temperature and does not require a temperature change, thus allowing a rapid reaction. The heating block is formed, for example, to have a structure as illustrated in FIGS. 22A and 22B so as to realize efficient heat transfer as mentioned above. Heating of the block may be performed using known methods in the art, and those skilled in the art will be able to select an appropriate method. For example, a Peltier element, a resistive heater, a heating coil, air having a specific temperature, or a high-temperature or low-temperature liquid may be used, without limitation thereto.

In the method according to the present invention, the reaction solution is the subject of temperature change. The PCR by the method according to the present invention may be rapidly performed compared to a conventional PCR on the basis of a general PCR execution volume of 20 µl under the assumption that a generally used polypropylene reaction vessel is used and currently used general conditions (tube and volume) are equally applied. In addition, the method of the present invention may also be applied when a reaction vessel, which is formed of any another material or any another shape (such as a microfluidic device) is used or when a reaction solution having a volume other than 20 µl is applied. In this case, the method may proceed quickly compared to a Peltier-based temperature control method using a single heating or cooling source.

When a different vessel or a different volume is applied, the ramping rate (the degree of temperature change per second) may vary due to the characteristics of the method of the present invention. The heating or cooling time may be experimentally determined by acquiring the ramping rate depending on a volume change or material characteristics.

In a first step of the method according to the present invention, a reaction vessel is brought into contact with a heating block, which is maintained at a temperature of about 100° C., for example, 95° C. required for denaturation of a nucleic acid, for a predetermined time. The term "predetermined time" as used herein means the time taken until the temperature of a reactant accommodated in a PCR tube widely used in a general PCR, for example, a thin-wall tube formed of polypropylene (e.g., MicroAmp® PCR tube of Thermo Fisher) reaches a temperature sufficient for the denaturation of a double-stranded DNA in a reaction solution via contact with the heating block, and may be determined in consideration of the volume of the reaction solution, and those skilled in the art will be able to select an appropriate time in consideration of specific reaction conditions. In one embodiment using the reaction solution having a volume of 20 µl, the contact time may range from 1 second to 15 seconds.

Figure 23A:
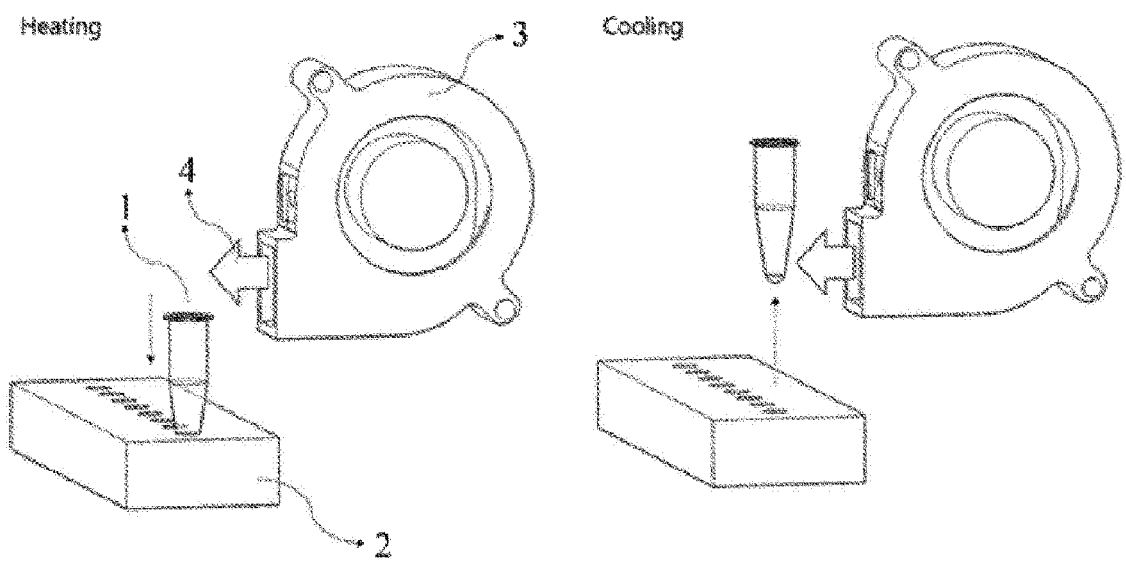
FIGS. 23A and 23B are views diagrammatically illustrating possible methods of achieving heating and cooling in the method according to the present invention, the left drawing illustrating that the reaction vessel 1 in which the reaction solution is accommodated moves to the heating block 2 so that the reaction solution is heated by contact between the reaction vessel and the heating block, and then the reaction vessel 1 moves to the front of the blower fan 3 so that the reaction solution is cooled by contact between the reaction vessel and the airflow 5 generated from the blower fan 3, and the right drawing illustrates the case in which heating is achieved by blowing and cooling is achieved by the block.
Figure 23B:
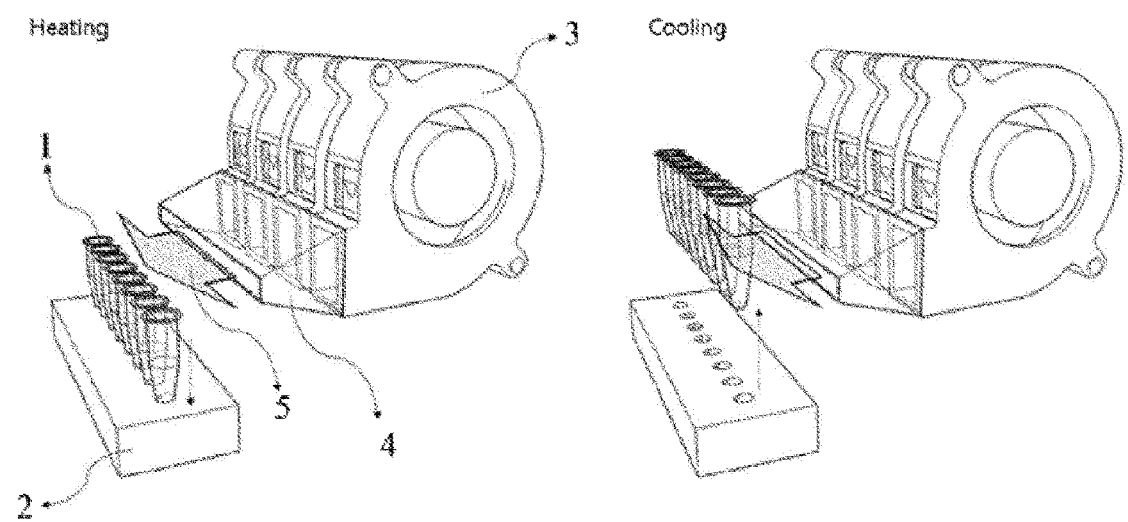

In the method according to the present invention, after the first step, the reaction vessel and the heating block are separated from each other by a predetermined distance. In this process, the heating block and/or the reaction vessel may be moved. As illustrated in FIG. 23, the heating block may be lowered or may be fixed, or the reaction vessel may be moved upward.

The distance is not particularly limited as long as the effect of the movement time on the total reaction time is minimized, and is determined so as to be suitable for exposure according to the position of a blower. Specifically, the distance is determined to prevent the temperature of the heating block from affecting the reaction vessel, for example, to allow the reaction vessel to be sufficiently spaced apart from the air around the heating block which is heated by the heating block and prevent a blown cooling airflow from reaching or coming into contact with the heating block and thus from having a negative effect on the maintenance of the temperature of the heating block. In one embodiment, the distance may range from 0.5 cm to 2 cm.

After the heating block and the reaction vessel are separated from each other, the reaction vessel may be exposed to an artificial airflow for a predetermined time for cooling in a second step. Alternatively, the reaction vessel may remain stationary in the air for a predetermined time. The former is used in a two-step reaction in which annealing and extension are performed in one step, and the latter is used in a three-step reaction in which annealing and extension are separately performed.

In one embodiment according to the present invention, annealing and extension are performed in one step, and the reaction vessel separated from the heating block is exposed to the artificial airflow for a predetermined time. The artificial airflow may be at room temperature, and may be provided by a fan-type device having a motor, for example, a general cooling fan, a blower fan, a cross fan, or an air compressor, without limitation thereto.

In the second step of the method in which annealing and extension are performed in one step according to the present invention, a predetermined contact time is determined according to a second target temperature, for example, 55° C. to 70° C. Herein, the predetermined time in the second step refers to the time during which the reactant comes into contact with the airflow to reach an annealing or extension reaction temperature and may be determined in consideration of the volume of the reaction solution, and those skilled in the art will be able to select an appropriate time in consideration of specific reaction conditions. In one embodiment using the reaction solution having a volume of 20 µl, the contact time may range from 1 second to 15 seconds.

Alternatively, in another embodiment according to the present invention, denaturation, annealing, and extension are performed, respectively. In this case, after a denaturation step performed at a first temperature, the heating block and the reaction vessel are separated from each other, and the reaction vessel is cooled to a second-first annealing temperature and then is heated again to a second-second elongation temperature. Thereafter, a third step of causing the reaction vessel to remain stationary at room temperature may be performed for a predetermined time.

In this case, the method according to the present invention is a temperature control method in a nucleic acid amplification reaction in which one cycle consisting of a denaturation step performed at a first temperature, an annealing step performed at a second-first temperature, and an extension step performed at a second-second temperature is repeated multiple times. The method includes a first step of heating a vessel used for a nucleic acid amplification reaction to a first temperature by bringing the vessel into contact with a heating block consistently maintained at the first temperature for a predetermined time, a second step of cooling the vessel to a second-first temperature by separating the vessel from the heating block by a predetermined distance so that the separated vessel is exposed to an artificial airflow for a predetermined time, and a third step of heating the vessel to a second-second temperature via contact between the vessel and the heating block for a predetermined time and thereafter, separating the heating block from the vessel by a predetermined distance to cause the separated vessel to remain stationary in the air for a predetermined time.

In the third step, the temperature of the reaction vessel is raised to an extension temperature, for example, 72° C. by the heating block, and thereafter, the reaction vessel is separated from the heating block and remains stationary in the air. The reaction vessel is brought into contact with the heating block twice, unlike the case in which annealing and extension are performed in one step, and the temperature of the reaction vessel may be adjusted by changing the contact time. For example, based on the volume of 20 µl, the heating block may come into contact with the reaction vessel for about 10 seconds to realize the denaturation temperature, for example, 91° C. in the first step, and may come into contact with the reaction vessel for about 3 seconds to realize the extension temperature, for example, 72° C. in the third step.

In the step of separating the heating block and the reaction vessel from each other, the heating block or the reaction vessel may be moved so that the reaction vessel is exposed, as described above. For a description of this step, refer to the above description.

While the exemplary embodiments of the present invention have been described in detail, it is to be understood that the scope of the present invention is not limited thereto and various modifications and improvements made by those skilled in the art using the basic concept of the present invention as defined in the following claims are also within the scope of the present invention.

Example 1: Temperature Control of Reaction Solution Based on Control of Contact Time of Heating Block and Reaction Vessel A high-speed temperature control method according to the present invention controls the temperature of a reaction vessel in which a reaction solution is accommodated by controlling the time of contact between a reaction vessel and a heating block or an airflow generated from a blower fan. With this method, the temperature of the reaction solution may be controlled to rapidly reach a target temperature.

In this example, a temperature measuring device was attached to the reaction vessel in which the reaction solution is accommodated, and the reaction vessel was repeatedly moved to the heating block or to the front of the blower fan so as to come into contact with the heating block or an airflow from the blower fan for a predetermined time. A change in the temperature of the reaction solution for each contact time was measured. The composition of the reaction solution, the reaction vessel, and the heating block were as follows:

Temperature measuring device: Pico technology (UK) TC-08 thermocouple data logger+thermocouple (K type); Reaction solution: 20 µl PCR buffer (10 mM Tris-HCl, pH 8.3+50 mM KCl+2 mM MgCl2); Reaction vessel: Bio-Rad 0.2 Ml tube strip (low profile); heating block: Bio-Rad c1000 thermal cycler (98° C. incubation setting); and blower fan: 3D-Manufactured 12 V, 0.15 A, and 1.8 W blower fan.

Figure 24:
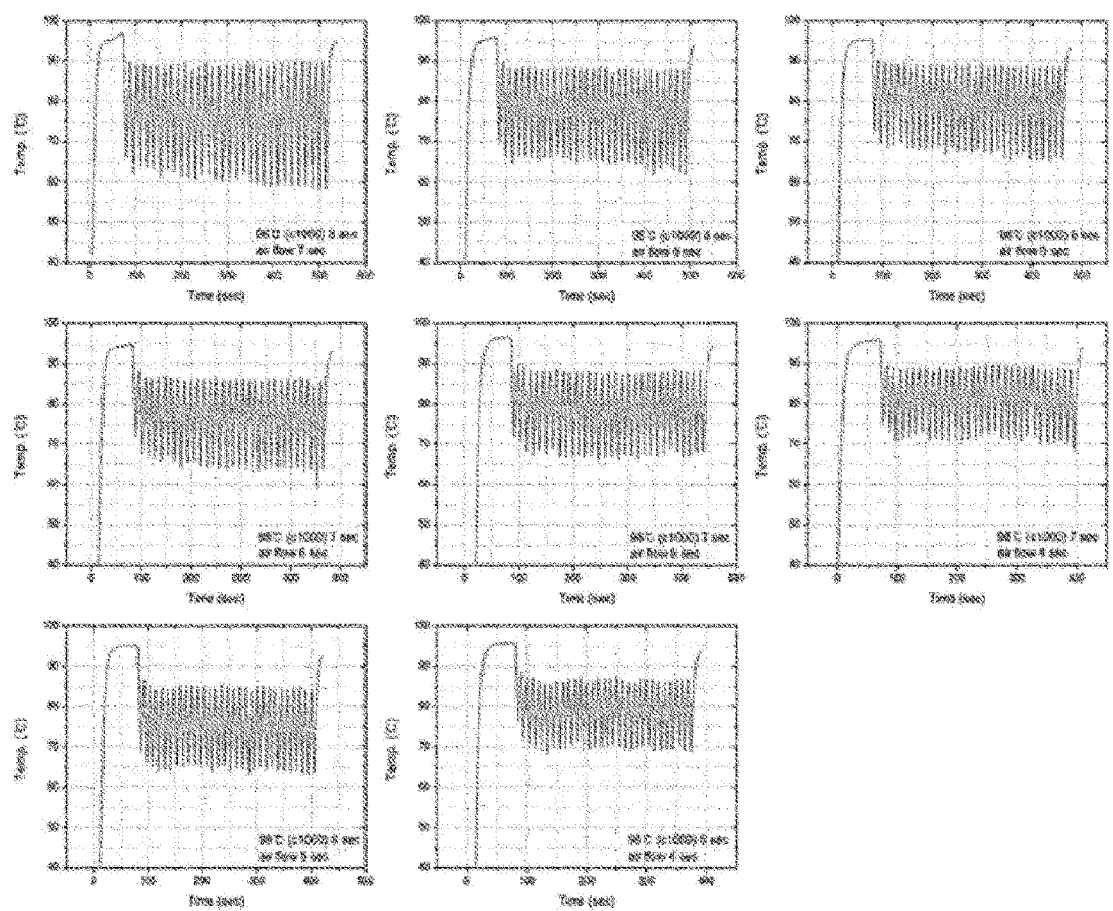
FIG. 24 illustrates a change in the temperature of the reaction solution when the method according to the present invention is performed, the results illustrating that the temperature may be changed within various ranges by controlling the contact time between the reaction vessel and a heating or cooling medium.

As a result, by controlling the contact time between the heating block and the cooling medium as illustrated in FIG. 24, it is possible to control the reaction solution to a target temperature within various ranges.

Figure 25:
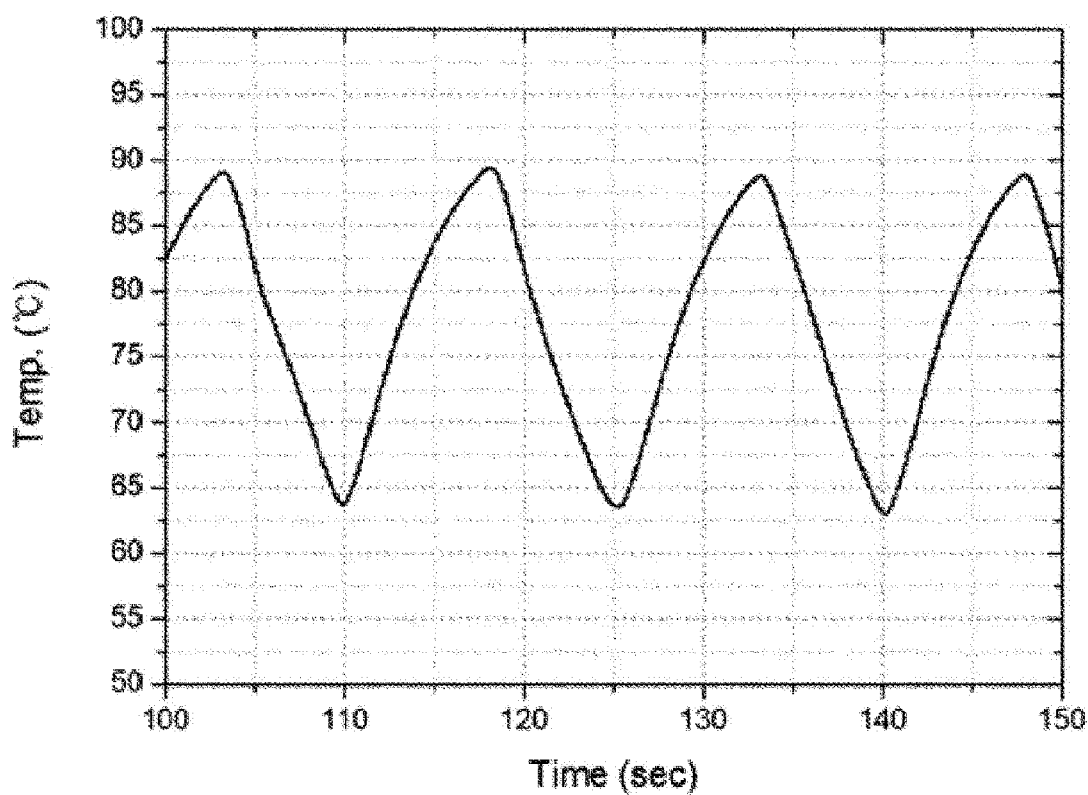
FIG. 25 illustrates the result of a change in the temperature of the reaction solution when a heating step for 8 seconds and a cooling step for 7 seconds are repeatedly performed in the method according to the present invention when the temperature of the reaction solution needs to be repeatedly changed within a temperature range of about 65° C. to 90° C.

In addition, repetitive temperature control is possible as illustrated in FIG. 25. In this example, repetitive temperature control was possible by repeating the process of setting a temperature change period of the reaction solution to 65° C. to 90° C., bringing the reaction vessel in which the reaction solution is accommodated into contact with the heating block for 8 seconds, and then bringing the reaction vessel into contact with the airflow generated by the blower fan for 7 seconds. At this time, the actually measured temperature result of the reaction solution was 63° C. to 89° C. At this time, the time taken until the temperature of the reaction solution changes from 63° C. to 89° C. and then again returns to 63° C. was 15 seconds, and the time taken to repeat the temperature change was only 7 minutes and 30 seconds. In contrast, in the case in which the reaction vessel is fixed to a block and the temperature of the block is changed to induce heating and cooling of a sample accommodated in the reaction vessel, even if an apparatus using a high-performance thermoelectric element (e.g., Bio-Rad c1000) was used, the time taken to repeat the aforementioned temperature change 30 times was about 16 minutes or more, which is twice the above time.

In the method according to the present invention, since the reaction vessel is quickly moved between the heating medium and the cooling medium, a relatively long time required for the temperature change of the heating medium or the cooling medium is not necessary, which allows the temperature change of a sample in the reaction vessel to be induced quickly, thus enabling a rapid reaction.

Figure 26:
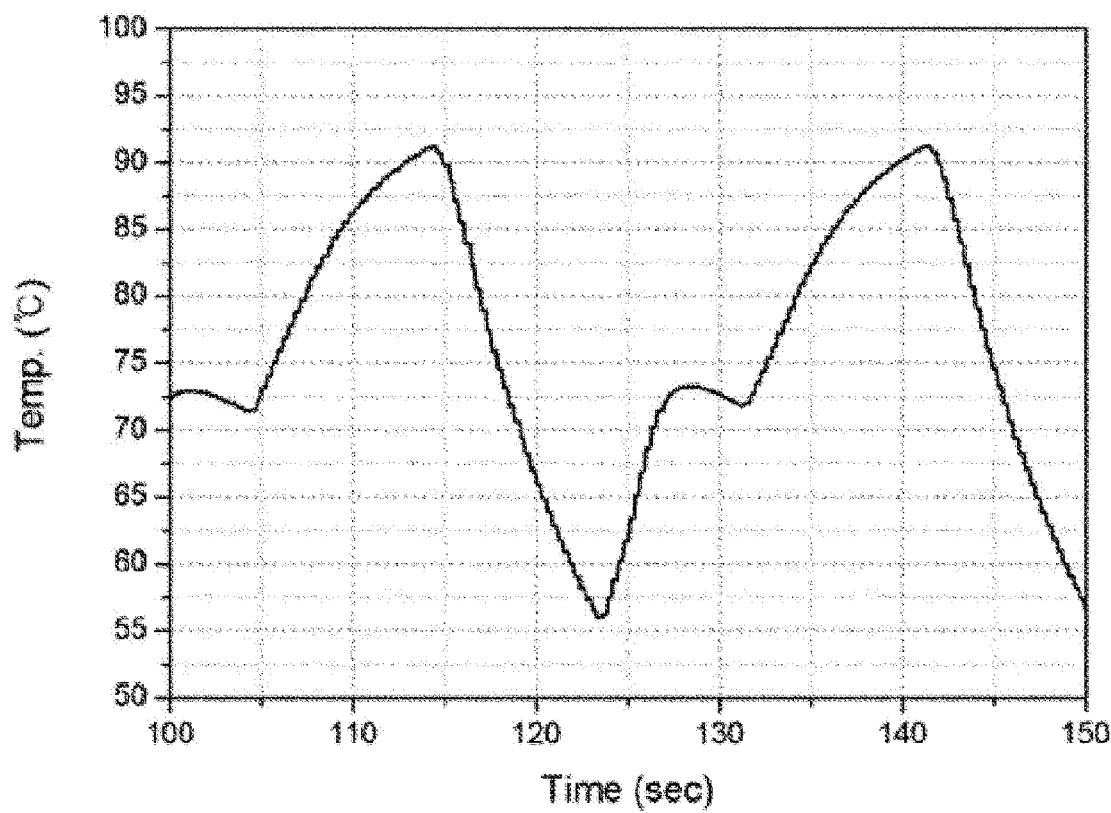
FIG. 26 illustrates a change in the temperature of the reaction solution as represented by 91° C.→56° C.→72° C.→91° C. when a heating step for 3 seconds, a stationary state for 5 seconds, a heating step for 10 seconds, and a cooling step for 9 seconds are repeatedly performed when three types of temperature changes are required in the method according to the present invention.

In addition, temperature change may be realized in three steps when a stationary step of separating a tube in which a reaction solution is accommodated from a heating block but preventing the tube from coming into contact with an airflow is provided during contact with the heating block and the airflow. FIG. 26 illustrates the case of heating the tube in which the reaction solution is accommodated by bringing the tube into contact with the heating block for 3 seconds, separating the tube from the heating block to cause the tube to remain stationary in the air for 5 seconds, and again bringing the tube into contact with the heating block for 10 seconds. For cooling, the tube was brought into contact with the airflow for 9 seconds. With this method, the reaction solution may reach three temperatures including 56° C. (annealing), 72° C. (extension), and 91° C. (denaturation).

Example 2. Detection of Target Nucleic Acid by High-Speed PCR Using Method According to Present Invention 2-1 *Mycoplasma* Pneumonia Detection A PCR mixture of 20 µl for the amplification of a *Mycoplasma* pneumonia sequence was added to a reaction vessel, and a process of bringing the reaction vessel into contact with a heating block for 8 seconds and with an airflow from a blower fan for 7 seconds was repeated 30 times. The reaction apparatus, the reaction conditions, and the composition of the reactant were as follows:

Reaction Vessel: Bio-Rad 0.2 Ml tube strip (low profile)
Heating Block: Bio-Rad c1000 thermal cycler (98° C. incubation setting)
Blower fan: 3D-Manufactured 12 V, 0.15 A, and 1.8 W blower fan
PCR Mixture Composition: forward and reverse primers, dNTP, PCR buffer (iNtRon), Taq polymerase (iNtRon), target DNA (*Mycoplasma* pneumonia cloned vector), enhancer, and evaGreen dye (Jena Bioscience)

```
Primer Sequence:
(forward)
5'-CAACCTCCATGTAGCTGATAG
or (reverse)
5'-GGTGATATCGCCAGGTAAA
```

High-Speed PCR Conditions: predenaturation 1 minute (98° C.), contact with the heating block (98° C.) for 8 seconds+contact with the airflow for 7 seconds, repetition of 30 times $10^5$~$10^1$ copies of a *mycoplasma* pneumonia target DNA were added respectively to reaction tubes, and negative control (NC) without a target DNA was also tested. After the high-speed PCR, amplification products were confirmed by melting curve analysis and electrophoresis, and the results are illustrated in FIGS. 27 and 28, respectively.

Figure 27:
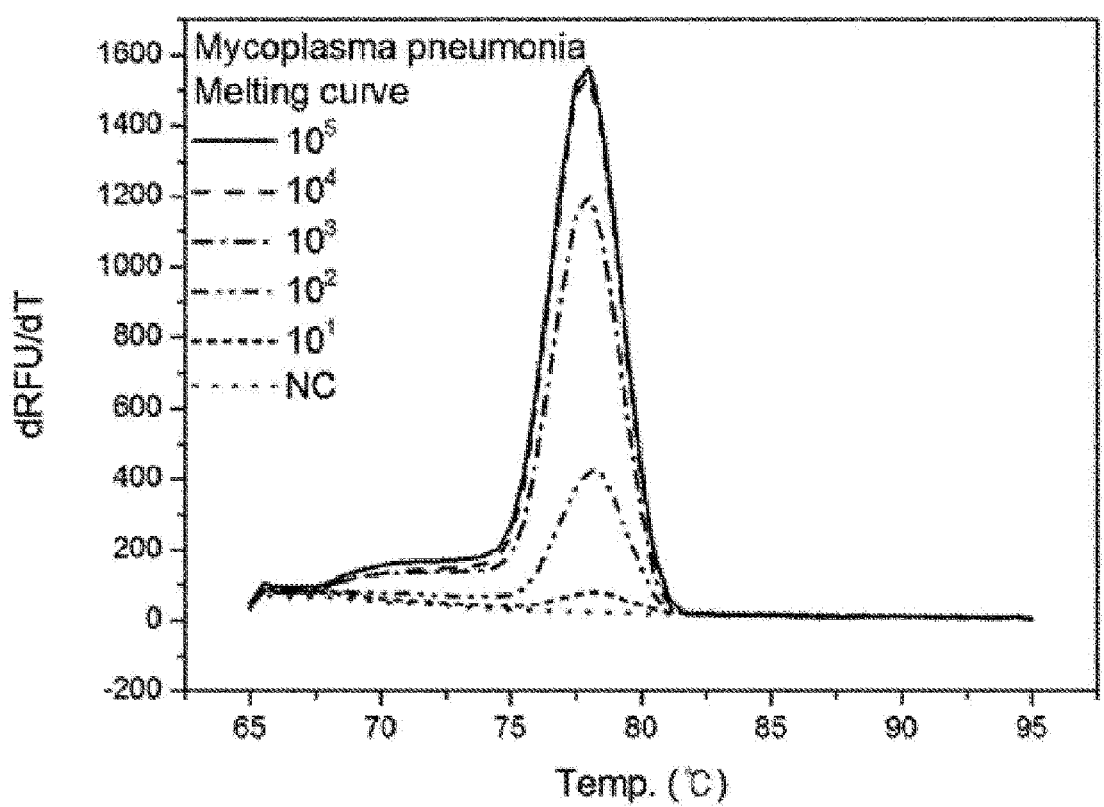
FIG. 27 illustrates that nucleic acids of various concentrations may be detected as a result of amplifying a *Mycoplasma* pneumonia cloned vector using the method according to the present invention, and thereafter inspecting the vector by melting curve analysis.
Figure 28:
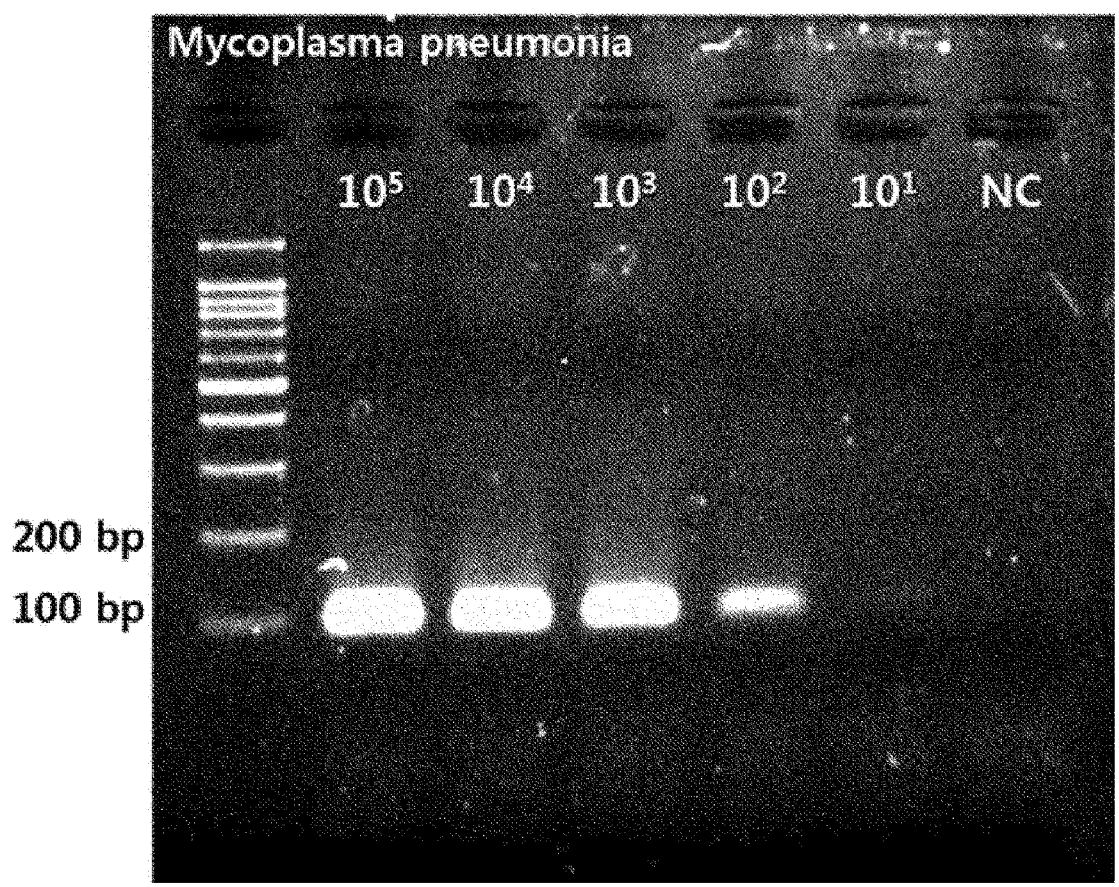
FIG. 28 is an electrophoresis gel photograph of a product produced by amplification performed according to FIG. 6, indicating that a target product is amplified correctly.

FIG. 27 is a melting curve analysis graph of a *mycoplasma* pneumonia high-speed PCR. No amplification product was detected in the NC tube having no target, the peak occurred from the case in which the amount of a target is 10 copies, and amplification was saturated at $10^4$ and $10^3$ copies. The electrophoresis gel photograph of FIG. 28 also illustrates the same results.

The time taken to repeat temperature change 30 times for a PCR in this example was 7 minutes and 30 seconds, and the time required for the entire PCR, including a predenaturation time of 1 minute before the PCR, was 8 minutes and 30 seconds. This is a very short time compared to a PCR method using a conventional PCR apparatus which requires 30 minutes or more.

2-2 HBV Detection

After preparing various concentrations of HBV sera by diluting an actual serum from an HBV patient, viral DNA was extracted from each serum and was mixed with a PCR solution. After the PCR solution of 20 µl to which each of viral DNAs of different concentrations had been added was added to a reaction tube strip to which PCR tubes were connected and tube caps were closed, a predenaturation step was performed for 1 minute using a heating block heated to 98° C. Next, a high-speed PCR was performed for HBV diagnosis by repeating the process of bringing the tubes into contact with the heating block for 8 seconds and bringing the tubes into contact with an airflow from a blower fan for 7 seconds 35 times. The reaction apparatus, the reaction conditions, and the composition of the reactant were as follows:

HBV gDNA extraction: Gene All Exgene viral DNA/RNA mini kit (128-150);

Reaction tubes: Bio-Rad 0.2 Ml tube strip (low profile);

Heating block: Bio-Rad c1000 thermal cycler (98° C. incubation setting);

Blower fan: four 3D-Manufactured blower fan of 12 V, 0.15 A, and 1.8 W+blower nozzle; PCR mixture composition: forward and reverse primers, dNTP, PCR buffer (iNtRon), Taq polymerase (iNtRon), target DNA (extracted *Mycoplasma* pneumonia gDNA), enhancer, and evaGreen dye (Jena Bioscience);

Primer sequence: 5'-GATGT'K'TCTGCGGCGTTTTATC (forward, 'K'=G or T) and 5'-CA'M'ACGGGCAACAT-ACCTTG (reverse, 'M'=A or C); and High-speed PCR: predenaturation 1 minute (98° C.), contact with the heating block (98° C.) for 8 seconds+ contact with the airflow for 7 seconds, repetition of 35 times.

Figure 29:
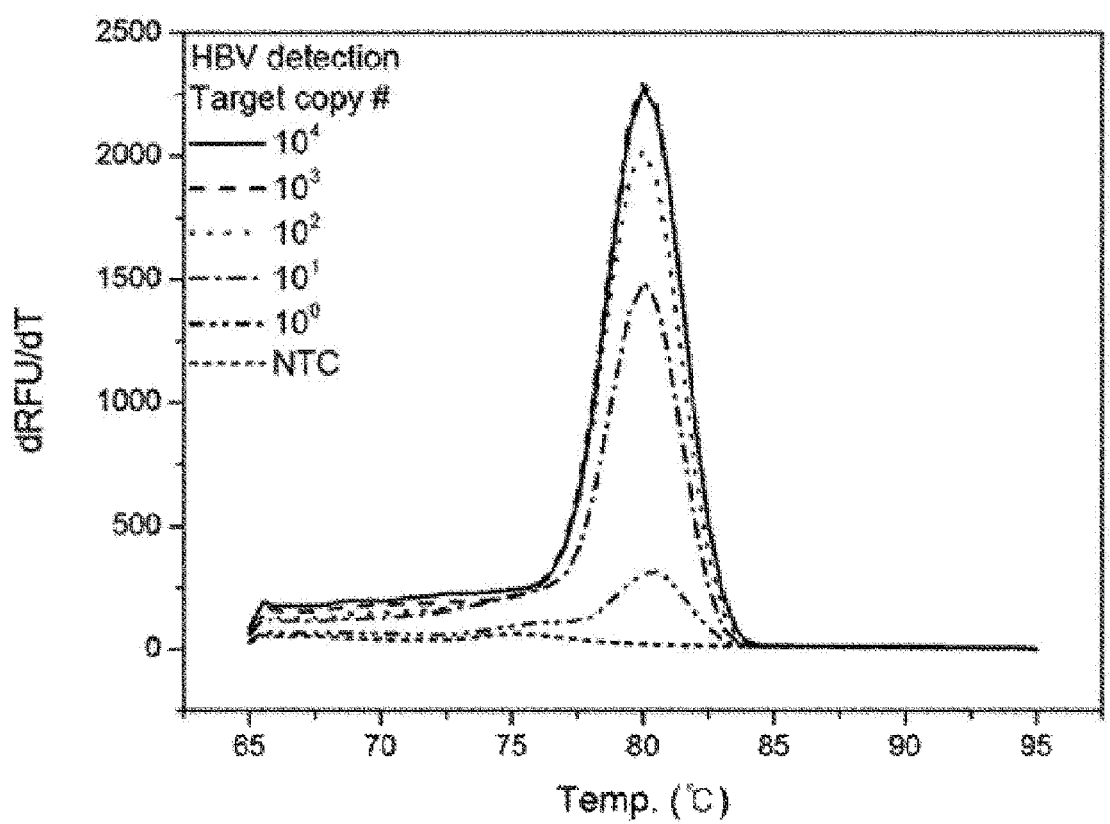
FIG. 29 illustrates that HBV of various concentrations may be detected as a result of amplifying a nucleic acid sample derived from an HBV patient using the method according to the present invention, and thereafter inspecting the sample by melting curve analysis.
Figure 30:
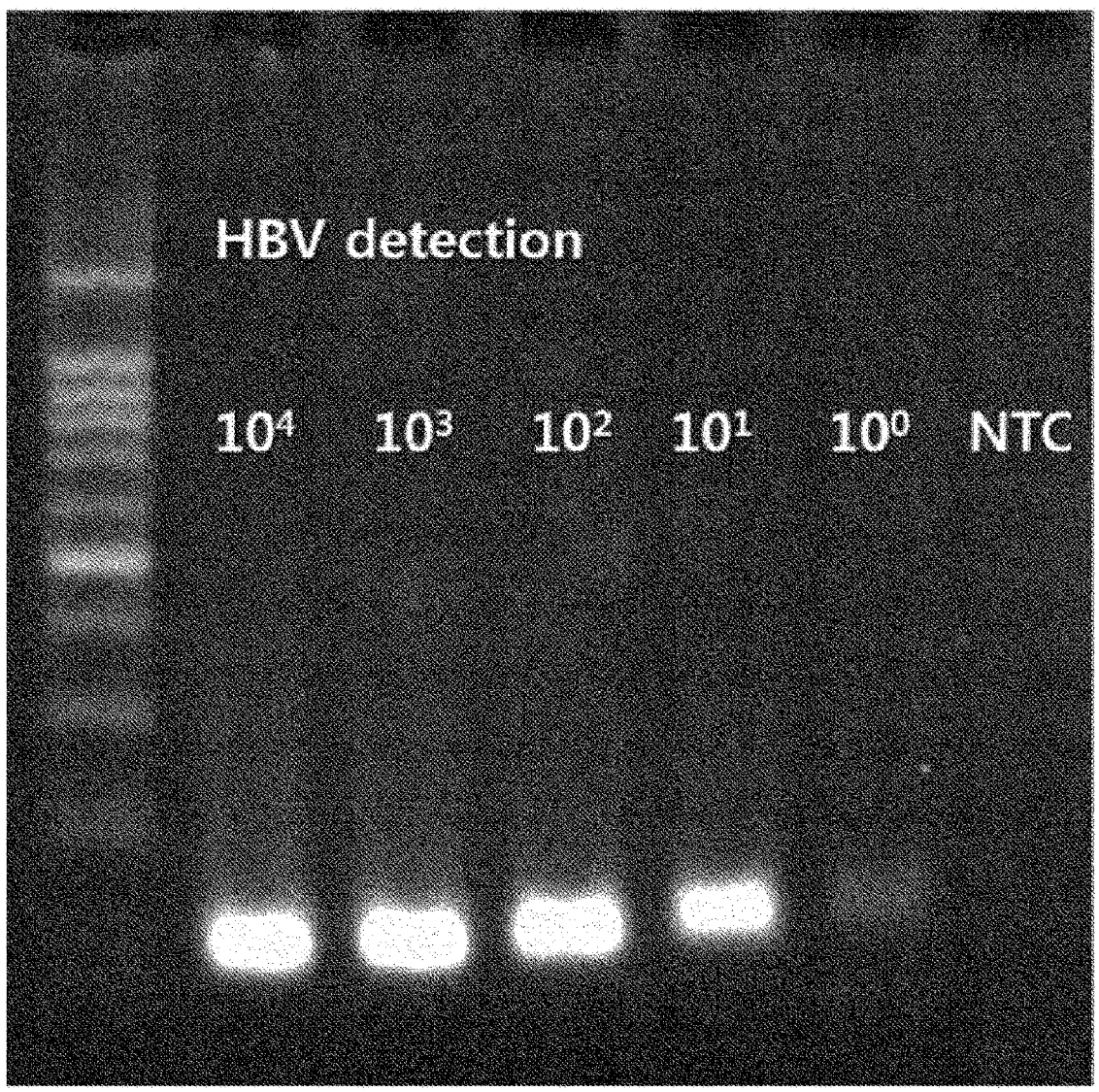
FIG. 30 is an electrophoresis gel photograph of a product by amplification performed according to FIG. 29, indicating that a target product is amplified correctly.

After the high-speed PCR, the amplification products were confirmed by melting curve analysis and electrophoresis, and the results are illustrated in FIGS. 29 and 30, respectively.

FIG. 29 is a graph illustrating melting curve analysis of a high-speed PCR amplification product for inspecting HBV infection. No HBV was detected as expected in an NTC tube in which a sample prepared by extraction of a normal sample which is not infected with HBV. In a sample collected from an actual HBV patient after dilution and viral DNA extraction, the marked peak of an amplification product occurred at the amount of a target of $10^4$ copies, and the height of the peak was gradually lowered as the dilution factor of the sample was increased. Thereby, 100 copies of HBV viral DNA could be detected. The electrophoresis gel photograph of FIG. 30 illustrates the same results.

The time required for a high-speed PCR for the diagnosis of HBV infection in this example was 8 minutes and 45 seconds, and the time required for the entire PCR including one minute of predenaturation before a PCR was 9 minutes and 45 seconds. This is a very short time compared to a general PCR-based method proposed by an HBV detection kit (Abbott Realtime HBV amplification reagent) using a conventional thermal cycler, which requires 1 hour and 50 minutes.

DESCRIPTION OF REFERENCE NUMERALS

1: conical tube in which a reaction solution is accommodated
2: heating block maintained at a high temperature
3: blower fan
4: blower nozzle
5: air (artificial airflow)
100: casing
110: lower plate
120: upper plate
122: introduction opening
124: fastener
130: side plate
140: display device
150: holder
152: holding body
154: mounting hole
156: fixing jig
160: hinge
170: signal input device
180: power supply device
200: heating module
210: heater
220: heating block
222: recess
224: light transmitting portion
230: guide unit
232: guide pipe
234: guide beam
236: elastic spring
240: opening and closing block
300: sensing module
310: module housing
312: module cover
314: module base
316: mounting wall
318: through-hole
320: light capturing unit
322: PCB
324: sensor
330: emission filter
400: drive module
410: motor
420: motor shaft
500: cooling module
510: blower fan
520: blower nozzle
522: inlet
524: outlet
600: cover module
610: cover housing
612: housing portion
614: opening and closing cover
620: cover base
622: filter insertion slot
624: light passage
630: light emitting unit
63 2: PCB
634: light source
640: tube cap heating element
642: through-hole
650: excitation filter
700: control device

The invention claimed is:

1. A high-speed nucleic acid amplification apparatus for use in a high-speed nucleic acid amplification reaction, the apparatus comprising:
a holder configured to fix a position of a tube in which a reaction occurs;
a heating module comprising a heater configured to generate heat so as to heat the tube and a heating block connected to the heater;
a drive module configured to vertically move the heating module so as to vary a distance between the heating module and the holder; and
a cooling module configured to cool the tube fixed to the holder, wherein:
the cooling module comprises a blower fan configured to generate a cooling airflow and a blower nozzle configured to transfer the cooling airflow generated by the blower fan to the tube fixed to the holder, and the blower nozzle is closed when the heating module is disposed adjacent to the holder and is opened when the heating module is spaced apart from the holder.

2. The apparatus according to claim 1, wherein:
the heating block is disposed below the holder and comprises at least one recess formed to allow at least a portion of the tube to be introduced thereinto; and
the drive module moves the heating block to vary a distance between the recess and the tube.

3. The apparatus according to claim 2, wherein:
the holder comprises at least one mounting hole vertically formed in the holder and having a predetermined inner diameter;
the tube is mounted in the mounting hole so that a lower portion of the tube is exposed downward; and
the lower portion of the tube is introduced into the recess when the heating block is raised, and the lower portion of the tube is spaced apart from the recess when the heating block is lowered.

4. The apparatus according to claim 1, wherein:
the heating module further comprises a guide unit disposed on a side of the heater; and
the guide unit comprises a guide pipe having a hole vertically formed therein, a guide beam inserted into the hole in the guide pipe to vertically extend, and an elastic spring located on the guide pipe so that the guide beam is inserted thereinto.

5. The apparatus according to claim 1, wherein:
the heating block is disposed below the holder;
the blower nozzle is disposed on one lateral side of the holder;
the heating module comprises an opening and closing block; and
the opening and closing block closes the blower nozzle when the heating block is raised, and is downwardly spaced apart from the blower nozzle to open the blower nozzle when the heating block is lowered.

6. The apparatus according to claim 3, wherein:
the holder comprises a plurality of mounting holes arranged in parallel to form one or more alignment lines;
the blower nozzle comprises an inlet adjacent to the blower fan and an outlet adjacent to the holder;
the outlet has a wider horizontal width than a horizontal width of the inlet; and
the outlet of the blower nozzle is horizontally disposed outside the holder, and the outlet has a width direction parallel to the alignment lines of the mounting holes.

7. The apparatus according to claim 1, further comprising:
a sensing module configured to sense a reaction signal of a reactant in the tube; and
a cover module disposed on the holder and configured to be opened or closed,
wherein the cover module comprises a light source configured to provide light to the tube, and the sensing module comprises a sensor configured to sense the light generated from the reactant in the tube.

8. The apparatus according to claim 7, wherein the cover module further comprises an excitation filter disposed below the light source, and the sensing module further comprises an emission filter disposed between the tube and the sensor.

9. The apparatus according to claim 7, wherein the heating block comprises a light transmitting portion formed in at least one direction so that the light generated in the tube is transmitted in at least one lateral direction.

10. The apparatus according to claim 1, further comprising a control device configured to control operations of the heating module, the drive module, and the cooling module.

11. A method of controlling a temperature of a nucleic acid amplification reaction in which denaturation performed at a first temperature and an annealing and extension reaction performed at a second temperature are repeated multiple times, the method comprising:
heating a reaction vessel, in which a reactant used for the nucleic acid amplification reaction is accommodated, to a first temperature by bringing the reaction vessel into contact with a heating block consistently maintained at the first temperature for a predetermined time; and
cooling the vessel to a second temperature by separating the vessel from the heating block by a predetermined distance so that the separated vessel is exposed to an artificial airflow for a predetermined time,
wherein the heating and the cooling are repeated multiple times with respect to the vessel cooled to the second temperature.

12. The method according to claim 11, wherein, in the cooling, the heating block is at a fixed position, and the vessel is moved upward of the heating block to a predetermined position so as to realize the predetermined distance.

13. The method according to claim 12, wherein the artificial airflow is continuously provided.

14. The method according to claim 11, wherein in the cooling, the vessel is at a fixed position, and the heating block is moved downward of the vessel to a predetermined position so as to realize the predetermined distance.

15. The method according to claim 14, wherein the artificial airflow is provided only when the heating block is spaced apart from the vessel by the predetermined distance.

16. The method according to claim 11, wherein the second temperature ranges from 55° C. to 70° C. to cause annealing and extension to occur at the same time.

17. The method according to claim 11, wherein the predetermined time in the cooling is determined as $t=4+2\times e^{-(v-7.4)/6.2}$, where t is the predetermined time and v is a velocity of the artificial airflow.

18. A method of controlling a temperature in a nucleic acid amplification reaction in which one cycle consisting of denaturation performed at a first temperature, annealing performed at a second-first temperature, and extension performed at a second-second temperature is repeated multiple times, the method comprising:
heating a vessel used for the nucleic acid amplification reaction to the first temperature by bringing the vessel into contact with a heating block consistently maintained at the first temperature for a predetermined time;
cooling the vessel to the second-first temperature by separating the vessel from the heating block by a predetermined distance so that the separated vessel is exposed to an artificial airflow for a predetermined time; and
heating the vessel to the second-second temperature by bringing the vessel into contact with the heating block for a predetermined time, and then separating the vessel from the heating block by a predetermined distance to cause the separated vessel to be kept stationary in air for a predetermined time,
wherein the heating, the cooling, and the keeping the vessel stationary are repeated multiple times.

19. The method according to claim 18, wherein, in the cooling or in the keeping the vessel stationary, when the vessel and the heating block are separated from each other by the predetermined distance, the heating block is at a fixed position, and the vessel is moved upward of the heating block to a predetermined position so as to realize the predetermined distance.

20. The method according to claim 19, wherein the artificial airflow is continuously provided.

21. The method according to claim 18, wherein, in the cooling or in the keeping the vessel stationary, when the vessel and the heating block are separated from each other by the predetermined distance, the vessel is at a fixed position, and the heating block is moved downward of the vessel to a predetermined position so as to realize the predetermined distance.

22. The method according to claim 21, wherein the artificial airflow is provided only when the heating block is spaced apart from the vessel by the predetermined distance.

23. The method according to claim 18, wherein the predetermined time in the cooling is determined as $t=4+2\times e^{-(v-7.4)/6.2}$, where t is the predetermined time and v is a velocity of the artificial airflow.

24. The method according to claim 11, wherein the predetermined distance ranges from 0.5 cm to 2 cm.

25. The method according to claim 19, wherein the predetermined time in the cooling is determined as $t=4+2\times e^{-(v-7.4)/6.2}$, where t is the predetermined time and v is a velocity of the artificial airflow.

26. The method according to claim 20, wherein the predetermined time in the cooling is determined as $t=4+2\times e^{-(v-7.4)/6.2}$, where t is the predetermined time and v is a velocity of the artificial airflow.

27. The method according to claim 21, wherein the predetermined time in the cooling is determined as $t=4+2\times e^{-(v-7.4)/6.2}$, where t is the predetermined time and v is a velocity of the artificial airflow.

28. The method according to claim 22, wherein the predetermined time in the cooling is determined as $t=4+2\times e^{-(v-7.4)/6.2}$, where t is the predetermined time and v is a velocity of the artificial airflow.

29. The method according to claim 18, wherein the predetermined distance ranges from 0.5 cm to 2 cm.

30. The method according to claim 12, wherein the predetermined time in the cooling is determined as $t=4+2\times e^{-(v-7.4)/6.2}$, where t is the predetermined time and v is a velocity of the artificial airflow.

31. The method according to claim 13, wherein the predetermined time in the cooling is determined as $t=4+2\times e^{-(v-7.4)/6.2}$, where t is the predetermined time and v is a velocity of the artificial airflow.

32. The method according to claim 14, wherein the predetermined time in the cooling is determined as $t=4+2\times e^{-(v-7.4)/6.2}$, where t is the predetermined time and v is a velocity of the artificial airflow.

33. The method according to claim 15, wherein the predetermined time in the cooling is determined as $t=4+2\times e^{-(v-7.4)/6.2}$, where t is the predetermined time and v is a velocity of the artificial airflow.

34. The method according to claim 16, wherein the predetermined time in the cooling is determined as $t=4+2\times e^{-(v-7.4)/6.2}$, where t is the predetermined time and v is a velocity of the artificial airflow.

* * * * *